United States Patent
Liang et al.

(10) Patent No.: US 11,739,339 B2
(45) Date of Patent: Aug. 29, 2023

(54) TRANSLATION CONTROL TOOL FOR PLANTS

(71) Applicant: The Regents of the University of California, Oakland, CA (US)

(72) Inventors: Yan Liang, Oakland, CA (US); Dominique Loque, Vernier (CH)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 224 days.

(21) Appl. No.: 15/645,877

(22) Filed: Jul. 10, 2017

(65) Prior Publication Data
US 2020/0332304 A1    Oct. 22, 2020

Related U.S. Application Data

(60) Provisional application No. 62/360,195, filed on Jul. 8, 2016.

(51) Int. Cl.
| | |
|---|---|
| *C12N 15/82* | (2006.01) |
| *C12N 9/22* | (2006.01) |
| *C12N 15/11* | (2006.01) |

(52) U.S. Cl.
CPC ........... *C12N 15/8213* (2013.01); *C12N 9/22* (2013.01); *C12N 15/11* (2013.01); *C12N 15/8216* (2013.01); *C12N 2310/20* (2017.05); *C12N 2800/80* (2013.01)

(58) Field of Classification Search
CPC combination set(s) only.
See application file for complete search history.

(56) References Cited

U.S. PATENT DOCUMENTS

| | | | | |
|---|---|---|---|---|
| 2014/0302563 | A1* | 10/2014 | Doudna | ................... C12P 19/34 435/91.51 |
| 2016/0053272 | A1* | 2/2016 | Wurtzel | ................. C12N 15/63 435/91.33 |

OTHER PUBLICATIONS

Murthy et al., "A nuclear micrococcal-sensitive, ATP-dependent exoribonuclease degrades uncapped but not capped RNA substrates." Nucleic Acids Res, 19, 2685-2692 (1991).
Hugouvieux et al., "Localization, ion channel regulation and genetic interactions during abscisic acid signaling of the nuclear mRNA cap-binding protein, ABH1." Plant Physiol, 130, 1276-1287 (2002).
Hugouvieux et al., "An mRNA cap binding protein, ABH1, modulates early abscisic acid signal transduction in *Arabidopsis*." Cell, 106, 477-487. (2001).
Gallie, "The cap and poly(A) tail function synergistically to regulate mRNA translational efficiency." Genes Dev, 5, 2108-2116. (1991).
Abramson et al., "Initiation factors that bind mRNA. A comparison of mammalian factors with wheat germ factors." J Biol Chem, 263, 5462-5467 (1988).
Frohberg et al., "Characterization of the interaction of plant transcription factors using a bacterial repressor protein." Proceedings of the National Academy of Sciences of the United States of America, 88, 10470-10474 (1991).
Weinmann et al., "A chimeric transactivator allows tetracycline-responsive gene expression in whole plants." Plant J, 5, 559-569. (1994).
Love et al., "Technical advance: stringent control of transgene expression in *Arabidopsis thaliana* using the Top10 promoter system." Plant J, 21, 579-588 (2000).
Moore et al., "A transcription activation system for regulated gene expression in transgenic plants." Proc Natl Acad Sci U S A, 95, 376-381 (1998).
Hickey et al., "Transgene regulation in plants by alternative splicing of a suicide exon." Nucleic Acids Res., 40, 4701-4710 (2012).
Rose, "The effect of intron location on intron-mediated enhancement of gene expression in *Arabidopsis*." Plant J, 40, 744-751 (2004).
Meshcheriakova et al., "Fine-tuning levels of heterologous gene expression in plants by orthogonal variation of the untranslated regions of a nonreplicating transient expression system." Plant Biotechnol J, 12, 718-727 (2014).
Kanoria et al., "A 28 nt long synthetic 5'UTR (synJ) as an enhancer of transgene expression in dicotyledonous plants." BMC Biotechnol, 12, 85 (2012).
Dugdale et al., "Design and construction of an in-plant activation cassette for transgene expression and recombinant protein production in plants." Nat. Protocols, 9, 1010-1027 (2014).
Mariani et al., "Induction of male sterility in plants by a chimeric ribonuclease gene." Nature, 347, 737-741 (1990).
Singh et al., "A novel male sterility-fertility restoration system in plants for hybrid seed production." Scientific Reports, 5, 1274 (2015).
Laubinger et al., "Dual roles of the nuclear cap-binding complex and SERRATE in pre-mRNA splicing and microRNA processing in *Arabidopsis thaliana*." Proc Natl Acad Sci U S A, 105, 8795-8800 (2008).
Nissim et al., Multiplexed and Programmable Regulation of Gene Networks with an Integrated RNA and CRISPR/Cas Toolkit in Human Cells. Mol. Cell, 54, 698-710 (2014).

(Continued)

*Primary Examiner* — Brent T Page
(74) *Attorney, Agent, or Firm* — Robin C. Chiang; Lawrence Berkeley National Laboratory

(57) ABSTRACT

The present invention provides for a system comprising (a) first polynucleotide encoding a first promoter operatively linked to an open reading frame (ORF) encoding an endoribonuclease, or an enzymatic active fragment thereof, which cleaves a cognition sequence (cog), and (b) a second polynucleotide encoding a second promoter operatively linked to a nucleotide sequence encoding (i) a cog linked to a coding sequence of interest (COI), (ii) a cog linked to the 3' end of a first COI and the 5' end of a second COI, or (iii) a cog locating within a LS (or targeting sequence) linked to a COI.

13 Claims, 13 Drawing Sheets
Specification includes a Sequence Listing.

(56) References Cited

OTHER PUBLICATIONS

Patron et al., "Standards for plant synthetic biology: a common syntax for exchange of DNA parts." The New phytol. 208, 13-19 (2015).
Liu et al., "Plant synthetic biology." Trends Plant Sci, 20, 309-317 (2015).
Gonzalez et al.,Tight regulation of plant immune responses by combining promoter and suicide exon elements. Nucleic Acids Res. 43: 7152-7161 (2015).
Brückner et al., A library of synthetic transcription activator-like effector-activated promoters for coordinated orthogonal gene expression in plants. The Plant Journal, 82: 707-713 (2015).
Chern et al., Overexpression of a rice NPR1 homolog leads to constitutive activation of defense response and hypersensitivity to light. Mol Plant Microbe Interact, 18, 511-520 (2005).
Voelker et al. Antisense down-regulation of 4CL expression alters lignification, tree growth, and saccharification potential of field-grown poplar. Plant Physiol, 154, 874-886 (2010).
Kasuga et al., Improving plant drought, salt, and freezing tolerance by gene transfer of a single stress-inducible transcription factor. Nat Biotech, 17, 287-291 (1999).
Hieno et al., ppdb: plant promoter database version 3.0. Nucleic Acids Res, 42, D1188-1192 (2014).
Lescot et al. PlantCARE, a database of plant cis-acting regulatory elements and a portal to tools for in silico analysis of promoter sequences. Nucleic Acids Res, 30, 325-327 (2002).
Liu et al., Computational discovery of soybean promoter cis-regulatory elements for the construction of soybean cyst nematode-inducible synthetic promoters. Plant Biotechnol J, 12, 1015-1026 (2014).
Bocobza et al., Small molecules that interact with RNA: riboswitch-based gene control and its involvement in metabolic regulation in plants and algae. Plant J, 79, 693-703. (2014).
Moore et al., Transactivated and chemically inducible gene expression in plants. The Plant Journal, 45, 651-683 (2006).
Coego et al., The TRANSPLANTA collection of *Arabidopsis* lines: a resource for functional analysis of transcription factors based on their conditional overexpression. Plant J, 77, 944-953. (2014).
Wilde et al., Control of gene expression in tobacco cells using a bacterial operator-repressor system. The EMBO journal, 11, 1251-1259 (1992).
Gatz et al. Stringent repression and homogeneous de-repression by tetracycline of a modified CaMV 35S promoter in intact transgenic tobacco plants. Plant J, 2, 397-404 (1992).
Bertrand et al., Overlapping divergent promoters control expression of Tn10 tetracycline resistance. Gene, 23, 149-156 (1983).
Mahfouz et al.,Targeted transcriptional repression using a chimeric TALE-SRDX repressor protein. Plant Mol Biol, 78, 311-321 (2012).
Guan et al., Heritable endogenous gene regulation in plants with designed polydactyl zinc finger transcription factors. PNAS, 99: 13296-13301 (2002).
Lowder et al., A CRISPR/Cas9 Toolbox for Multiplexed Plant Genome Editing and Transcriptional Regulation. Plant Physiol, 169, 971-985 (2015).
Zhang et al., Plant microRNA: A small regulatory molecule with big impact. Dev. Biol., 289, 3-16.(2006).
Ossowski et al., Gene silencing in plants using artificial microRNAs and other small RNAs. Plant J, 53, 674-690 (2008).
Zhou et al., MicroRNA-mediated gene regulation: potential applications for plant genetic engineering. Plant Mol Biol, 83, 59-75. (2013).
Brown et al., Endogenous microRNA can be broadly exploited to regulate transgene expression according to tissue, lineage and differentiation state. Nat Biotech, 25, 1457-1467 (2007).
Seyhan, A multiplexed miRNA and transgene expression platform for simultaneous repression and expression of protein coding sequences. Molecular bioSystems, 12, 295-312 (2016).
Brosnan et al., Cell-to-cell and long-distance siRNA movement in plants: mechanisms and biological implications. Curr. Opin. Plant Biol., 14, 580-587 (2011).
Van Dongen et al., Detecting microRNA binding and siRNA off-target effects from expression data. Nat. Methods, 5, 1023-1025 (2008).
Cerny et al., RNA-binding protein-mediated translational repression of transgene expression in plants. Plant Mol Biol, 52, 357-369. (2003).
Haurwitz et al., Sequence- and Structure-Specific RNA Processing by a CRISPR Endonuclease. Science, 329, 1355-1358 (2010).
Haurwitz, R.E., Sternberg, S.H. and Doudna, J.A. (2012) Csy4 relies on an unusual catalytic dyad to position and cleave CRISPR RNA. (2012).
Sternberg et al., Mechanism of substrate selection by a highly specific CRISPR endoribonuclease. RNA, 18, 661-672. (2012).
Qi et al., RNA processing enables predictable programming of gene expression. Nat Biotech, 30, 1002-1006. (2012).
Du et al., "Engineering Translational Activators with CRISPR-Cas System." ACS Synth Biol.5:74-80 ((2015).
Borchardt et al., "Controlling mRNA stability and translation with the CRISPR endoribonuclease Csy4." RNA, 21, 1921-1930. (2015).
Eudes et al., Expression of a bacterial 3-dehydroshikimate dehydratase reduces lignin content and improves biomass saccharification efficiency. Plant Biotechnol J, 13, 1241-1250. (2015).
Ham et al., "Design, implementation and practice of JBEI-ICE: an open source biological part registry platform and tools." Nucleic Acids Res, 40, e141. (2012).
Sparkes et al., "Rapid, transient expression of fluorescent fusion proteins in tobacco plants and generation of stably transformed plants." Nat Protoc., 1, 2019-2025 (2006).
Clough et al., "Floral dip: a simplified method for Agrobacterium-mediated transformation of *Arabidopsis thaliana*." Plant J, 16, 735-743 (1998).
Kanehisa et al., "KEGG as a reference resource for gene and protein annotation." Nucleic Acids Res, 44, D457-462. (2016).
Grissa et al., "The CRISPRdb database and tools to display CRISPRs and to generate dictionaries of spacers and repeats." BMC Bioinformatics, 8, 172. (2007).
Chen et al., "A highly efficient transient protoplast system for analyzing defence gene expression and protein-protein interactions in rice." Mol. Plant Pathol., 7, 417-427. (2006).
Visa et al., (1996) A nuclear cap-binding complex binds Balbiani ring pre-mRNA cotranscriptionally and accompanies the ribonucleoprotein particle during nuclear export. The Journal of Cell Biology, 133, 5-14.
Fuke et al., "Role of poly (A) tail as an identity element for mRNA nuclear export." Nucleic Acids Res., 36, 1037-1049 (2008).
Bell-Lelong et al., "Cinnamate-4-Hydroxylase Expression in *Arabidopsis* (Regulation in Response to Development and the Environment)." Plant Physiol., 113, 729-738 (1997).
Ebert et al., "Identification of an essential upstream element in the nopaline synthase promoter by stable and transient assays." Proc Natl Acad Sci U S A, 84, 5745-5749 (1987).
Aoyama et al., "A glucocorticoid-mediated transcriptional induction system in transgenic plants." Plant J, 11, 605-612. (1997).
Padidam, "Chemically regulated gene expression in plants." Curr Opin Plant Biol, 6, 169-177 (2003).
Cazzonelli et al., "An in vivo, luciferase-based, Agrobacterium-infiltration assay system: implications for post-transcriptional gene silencing." Planta, 224, 582-597 (2006).
Yang et al, "Isolation of a strong *Arabidopsis* guard cell promoter and its potential as a research tool." Plant methods, 4, 6 (2008).
Dong et al., "PlantGDB, plant genome database and analysis tools." Nucleic Acids Res, 32, D354-359. (2004).
Duvick et al., "PlantGDB: a resource for comparative plant genomics." Nucleic Acids Res., 36, D959-D965. (2008).
Smanski et al., "Synthetic biology to access and expand nature's chemical diversity." Nat Rev Micro, 14, 135-149. (2016).
Jansen, "mRNA localization: message on the move." Nat Rev Mol Cell Biol, 2, 247-256. (2001).

\* cited by examiner pAct2::cogRFP+p35S::cogGFP

GFP Scan

RFP Scan

+Csy4  -Csy4

TRANSLATION CONTROL TOOL FOR PLANTS

RELATED APPLICATIONS

The application claims priority to U.S. Provisional Patent Application Ser. No. 62/360,195, filed Jul. 8, 2016, which is herein incorporated by reference in its entirety.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of plant gene expression.

BACKGROUND OF THE INVENTION

For three decades, plant transgenic techniques have been widely used in basic biological research, supporting plant-based metabolic engineering and improving agronomic traits in crops. For some of these applications, such as herbicide resistance, constitutive expression of transgenes is acceptable. In many other cases, however, tight and/or synchronized transgene expression is highly preferable (1,2). For example, ectopic expression of transgenes and leakiness of promoters may be detrimental to host plants if the transgene product is toxic or affects several metabolic pathways non-specifically (3-5). Improved precision in transgene expression is essential for advances in bioengineering. In addition to alleviating potential toxicity, it allows better control of carbon and metabolite fluxes, and supports the development of complex pathways and traits.

In plant research, most efforts to control transgene expression are limited to a small number of tissue-specific promoters that have been characterized and documented (6,7). Few natural and synthetic promoters have been developed to drive transgene expression in response to environmental (5,8), metabolic (9) or chemical stimuli (10,11). Robust and versatile tools, that function as "switch off" devices to repress transgene expression, are still lacking. In bacterial operons, repressor proteins bind to operator sequences and repress transcription. In tobacco plants, when the bacterial LacO and TetO operator sequences were inserted into plant promoters, the downstream reporter expression was repressed up to 10-fold, and to 100-fold in the presence of repressor proteins LacI and TetR, respectively. (12,13). Because repression by LacI and TetR can be reversed in the presence of their specific ligands—lactose analogues (14) and tetracyclin (15), respectively—the LacO and TetO operators and their variants were originally developed for bacterial expression systems to control the induction of transgene expression upon ligand supply (12,13). Engineered DNA binding proteins—such as zinc fingers, transcription activator-like effectors, and more recently the inactivated CRISPR/CAS9 system (dCAS9) fused to a repressor domain (e.g. SRDX)—allow specific transcription inhibition (16-18). In addition, regulation strategies at the post-transcriptional level are being developed to layer gene regulation, further improve expression tightness, and offer greater options to control transgene products. MicroRNAs mediate a vast post-transcriptional network for the regulation of plant development, physiology, and defense (19). MicroRNA-based gene silencing is a potent transgenic technique for plant trait improvement (20,21). In mammalian cells, microRNAs have been exploited to increase the stringency of transgene regulation (22,23). While microRNAs and engineered DNA-binding proteins are critical tools for the manipulation of endogenous gene expression, their utility for transgene regulation is limited because, for each transgene target, specific microRNA or gRNA sequences need to be designed and tested for efficiency. Moreover, the free-diffusion property of microRNAs (24) compromises tissue-specific repression and adds to the risk of off-target effects (25). At the translational level, an RNA-binding protein was adopted from coliphages and yeast for transgene repression (26). A drawback of the latter system is that, for efficient repression, the repressor protein must be expressed several times more than the target mRNA to be regulated (26).

SUMMARY OF THE INVENTION

The present invention provides for a system comprising (a) first polynucleotide encoding a first promoter operatively linked to an open reading frame (ORF) encoding (i) optionally a localization signal (LS) and (ii) an endoribonuclease, or an enzymatic active fragment thereof, which cleaves a cognition sequence (cog), wherein the LS is linked to the 5' end of the endoribonuclease; (b) a second polynucleotide encoding a second promoter operatively linked to a nucleotide sequence encoding (i) a cog linked to a coding sequence of interest (COI), (ii) a cog linked to the 3' end of a first COI and the 5' end of a second COI, or (iii) a cog locating within a LS (or targeting sequence) linked to a COI; and optionally one or more (c) third polynucleotide encoding a third promoter operatively linked to a nucleotide sequence encoding (i) a cog linked to a coding sequence of interest (COI), (ii) a cog linked to the 3' end of a COI and the 5' end of a second COI, or (iii) a cog locating within a LS (or targeting sequence) linked to a COI. In some embodiments, the COIs of the third polynucleotide(s) are different from the COI(s) of the second polynucleotide.

In some embodiments, the LS is a nuclear localization signal (NLS). In some embodiments, the LS is a localization signal that localizes the expressed COI to a location, such as cytosol, plastid, or mitochondria.

The endoribonuclease can be any suitable endoribonuclease which cleaves a specific cog. In some embodiments, the cog when in a transcript forms a hairpin. In some embodiments, the endoribonuclease is an endoribonuclase encoded by one of the genes listed in FIG. 11. In some embodiments, the endoribonuclease is an endoribonuclase encoded by one of the genes listed in FIG. 11 from *Shewanella* sp. csy4 and clockwise to *Lactobacillus fermentum* casE. In some embodiments, the endoribonuclease is one selected from the group consisting of *Pseudomonas aeruginosa* Csy4, *Moraxella catarrhalis* Csy4, *Escherichia coli* CasE, *Verrucosispora maris* CasE, *Lactobacillus delbrueckii* CasE, and *Thauera aminoaromatica* CasE. In some embodiments, the endoribonuclease is one selected from the group consisting of *Shewanella piezotolerans* Csy4, *Pseudomonas aeruginosa* Csy4, *Selenomonas ruminantium* Csy4, *Psychrobacter* sp. Csy4, and *Acinetobacter baumannii* Csy4. In some embodiments, the endoribonuclease is a Csy4. In some embodiments, the Csy4 is *Pseudomonas aeruginosa* Csy4. In some embodiments, suitable endoribonucleases and corresponding target polyribonucleotides are disclosed in U.S. Pat. No. 9,115,348, hereby incorporated by reference. In some embodiments, the endoribonuclease is an endoribonuclease disclosed in U.S. Pat. No. 9,115,348. Table 3 provides a list of Csy4 orthologs and their corresponding recognition sequences.

TABLE 3

Putative targeting sequence of Csy4 orthologs.

| Csy4 Orthologs | GenBank Accession | Putative Recognition Sequence | |
|---|---|---|---|
| ND02 | WP 013439422 | GTATTCCCCACGCAAGTGGGGGTGATCC | SEQ ID NO: 42 |
| MZ1T | WP 012585437 | GGTTCCCCCGCGTCCGCGGGGATAGGCCC | SEQ ID NO: 43 |
| MG1655 | NP 417236 | GAGTTCCCCGCGCCAGCGGGGATAAACCG | SEQ ID NO: 44 |
| BB18 | WP 013107622 | TTCTAAGCGACCTGTGCGGTCGTGAAG | SEQ ID NO: 45 |
| AB18 | WP 013733009 | GGATCACCCCCGCGTGCGCGGGGAGCAG | SEQ ID NO: 46 |
| RP62 | WP 002486027 | GTTCTCGTCCCCTTTTCTTCGGGGTGGGTATCGATCC | SEQ ID NO: 47 |

In some embodiments, any two of or all three of the first, second, and third polynucleotides are the same polynucleotide, i.e. the polynucleotide encodes the elements of any two of or all three of the first, second, and third polynucleotides.

The present invention also provides for one or more nucleic acids encoding the system of the present invention. In some embodiments, each nucleic acid is vector capable of stable maintenance in a host cell. The host cell is a eukaryotic cell. The host cell can be an animal or plant cell. The host cell can be a mammalian, insect, or yeast cell. In some embodiments, the vector comprises nucleotide sequences which enable its stable maintenance in the host cell or integration into the genome of the host cell. The nucleic acid can further comprises transcriptional control sequences, such as a promoter, activation sequences, or the like, which enable the expression of the encoded polypeptide in the host cell. One skilled in the art is able to determine what sequences to use in a particular host cell. In some embodiments, the host cell is a plant cell, or a plant cell in a plant.

The present invention also provides for a method of constructing the system, or a polynucleotide, of the present invention.

The present invention also provides for a plant comprising a genetically modified plant cell expressing the system of the present invention.

In some embodiments, the present invention increases the expression flexibility of transgenes by regulating mRNA translation in eukaroyotic host cells, such as plant cells. In some embodiments, the present invention is based on a two-component system and has at least three applications: (1) controlled disabling of the translation of a monocistronic gene by nuclear mRNA decapping to reduce or block nuclear export of a target mRNA and inhibit translation initiation (cleavage of engineered 5' UTR) (see FIG. 1A), (2) controlled enabling of the translation of a second cistron of a bicistronic gene (or the second and/or third cistron of a tricistronic gene, or any, some, or all cistrons, except the first cistron of a polycistronic gene) by cystolic cleavage of an engineered inter-cistronic region of the bistronic mRNA (or tricistronic or polycistronic mRNA) to be translated (see FIG. 1B), and (c) controlled dual targeting of a protein (such as, plastid/cytosol, mitochondria/cytosol, or nucleus/cytosol) by cytosolic cleavage of engineered mRNA harboring a sequence necessary for organelle targeting (see FIG. 1C).

The present invention provides for a system comprising a second polynucleotide encoding a second promoter operatively linked to a nucleotide sequence encoding (i) a cog linked to a coding sequence of interest (COI), (ii) a cog linked to the 3' end of a first COI and the 5' end of a second COI, or (iii) a cog locating within a LS (or targeting sequence) linked to a COI.

In some embodiments, the second polynucleotide encodes a second promoter operatively linked to a nucleotide sequence encoding (i) a cog linked to a coding sequence of interest (COI); wherein when the nucleotide sequence is transcribed into a transcript, the transcript comprises from 5' to 3': a 5' Cap, a 5' UTR (untranslated region), the cog, the COI, a 3' UTR, and a poly-A tail.

In some embodiments, the second polynucleotide encodes a second promoter operatively linked to a nucleotide sequence encoding (ii) a cog linked to the 3' end of a first COI and the 5' end of a second COI; wherein when the nucleotide sequence is transcribed into a transcript, the transcript comprises from 5' to 3': a 5' Cap, a first 5' UTR (untranslated region), the first COI, a first 3' UTR, the cog, a second 5' UTR, the second COI, a second 3' UTR, and a poly-A tail.

In some embodiments, the second polynucleotide encodes a second promoter operatively linked to a nucleotide sequence encoding (iii) a cog locating within a LS (or targeting sequence) linked to a COI; wherein when the nucleotide sequence is transcribed into a transcript, the transcript comprises from 5' to 3': a 5' Cap, a 5' UTR (untranslated region), a targeting sequence with the cog located within the targeting sequence, the COI, a 3' UTR, and a poly-A tail.

In some embodiments, the invention improves gene expression tightness (two-component expression system), DNA compaction for genetic engineering (reducing the number of promoters and terminators with polycistronic genes), gene expression synchronization (positive co-regulation of polycistronic genes, or negative co-regulation of more than one, or more than two, monocistronic genes), and/or engineering of compartmentalized metabolic pathways.

In some embodiments, the invention comprises the use of an endoRNase (such as Csy4) and its corresponding specific target site, which allows engineered mRNA with different components that can be processed (such as cleaved) as desired. In some embodiments, the invention comprises the use of a CRISPR-based RNA cleavage (Csy4 and its cognition sequence), or a similar endoRNase that has a biological activity identical to or similar to Csy4.

The invention is useful to engineer plants for biofuel purposes and fine tune protein expression. In some embodiments, it expresses polycistronic genes and synchronizes protein expression. It provides an expression repressor system and permits protein dual targeting.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
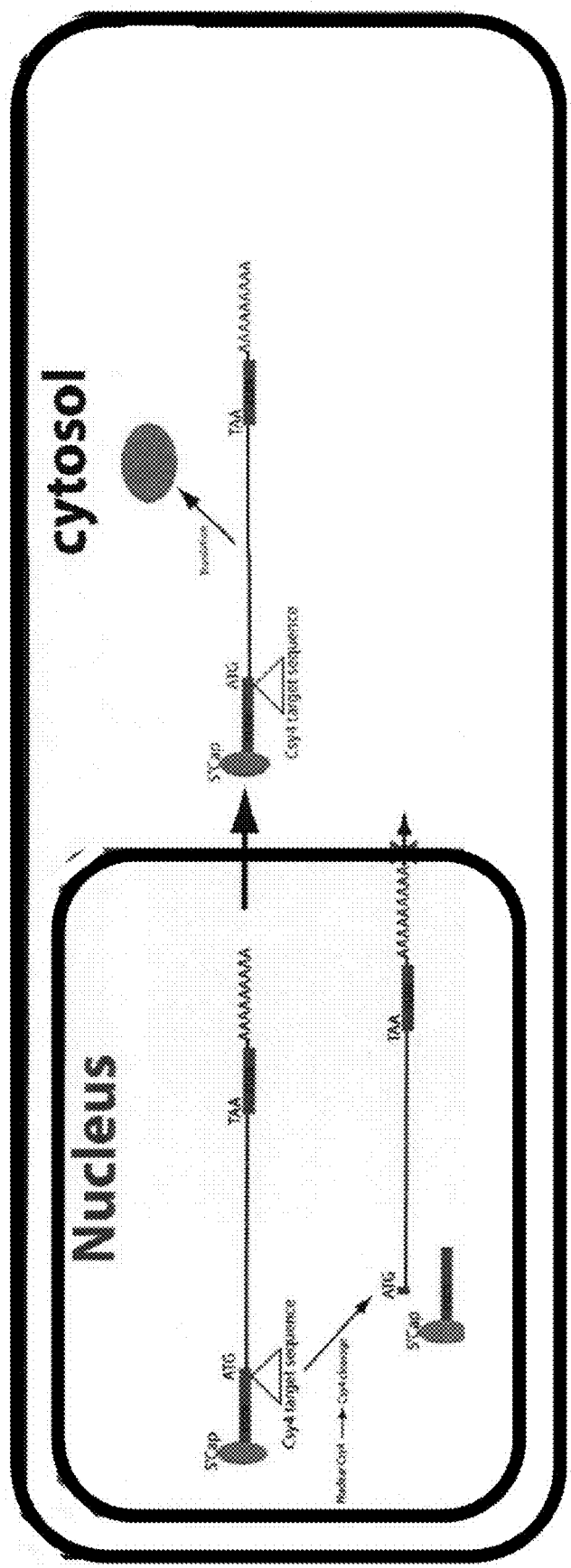
FIG. 1A. Illustration of an embodiment of the present invention.
Figure 1B:
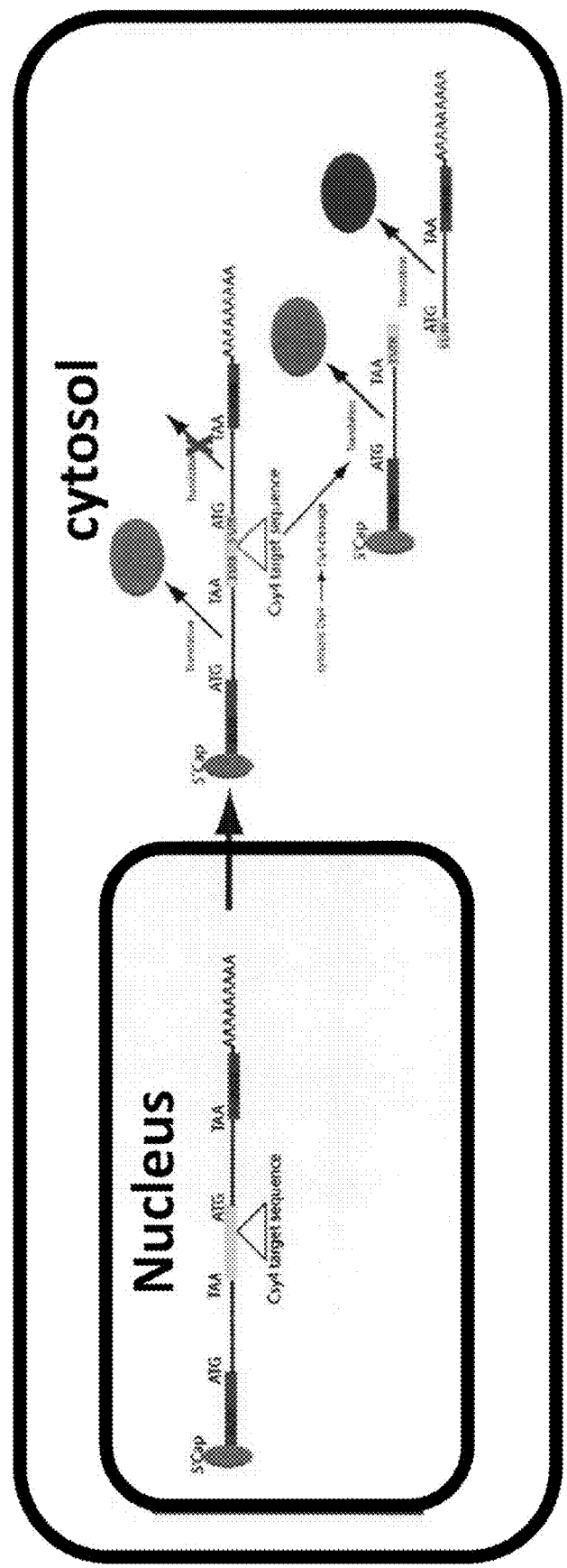
FIG. 1B. Illustration of another embodiment of the present invention.
Figure 1C:
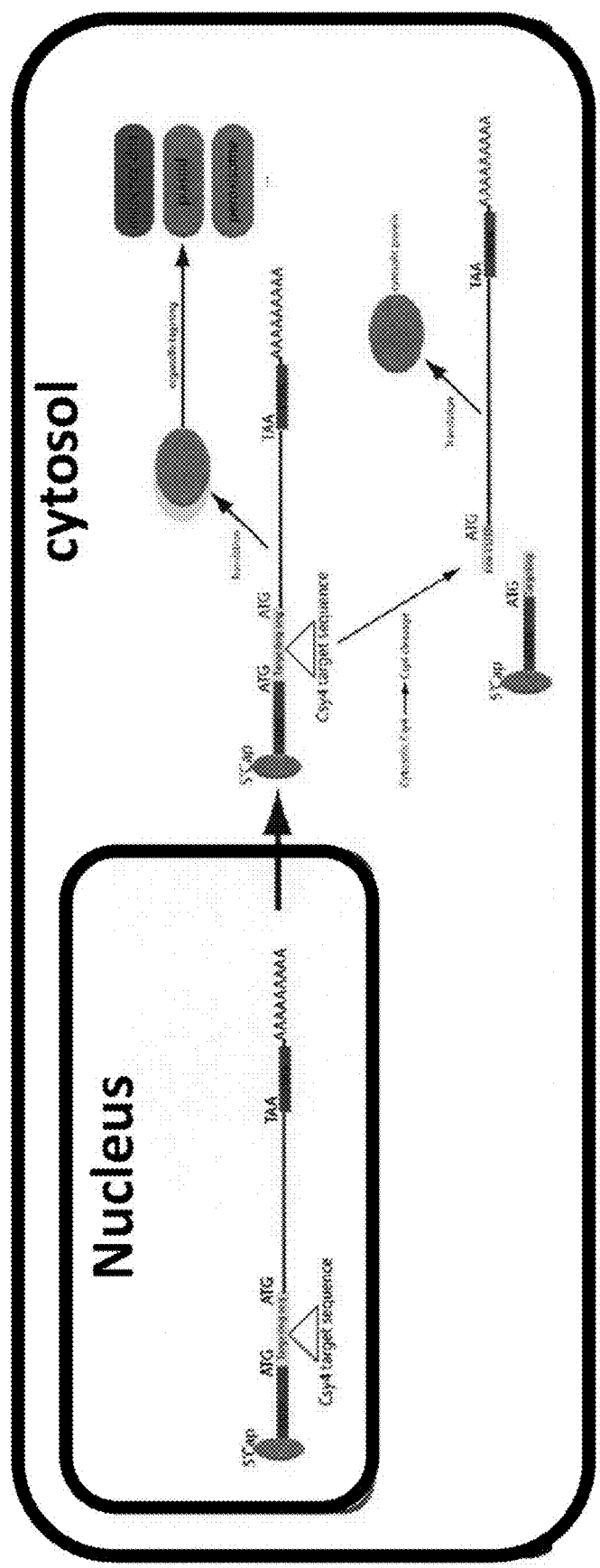
FIG. 1C. Illustration of another embodiment of the present invention.
Figure 1D:
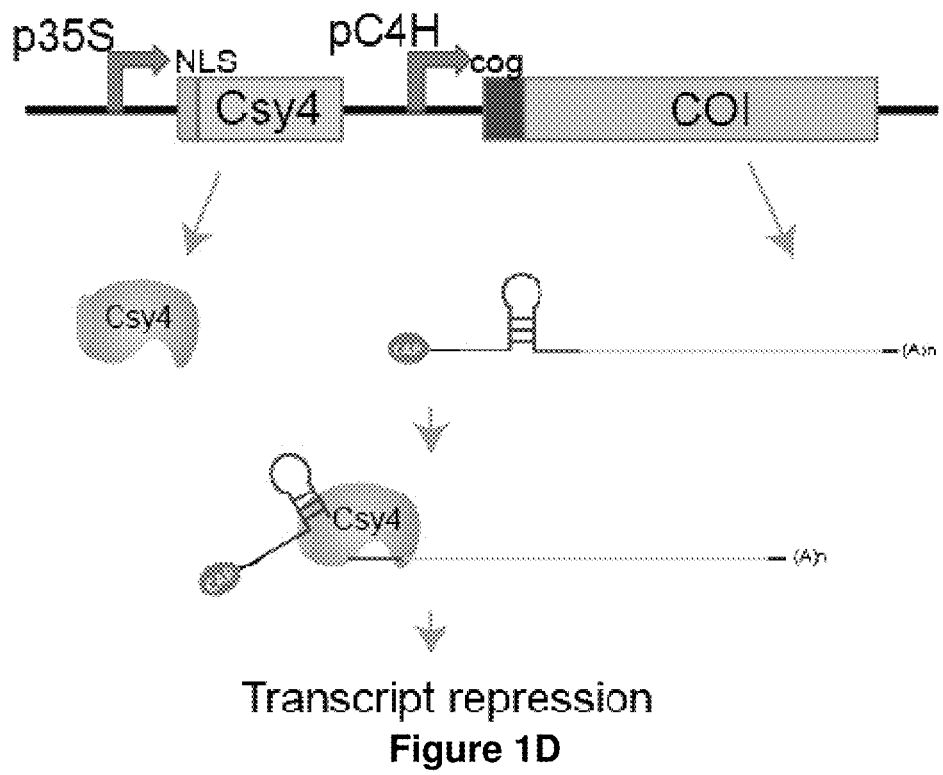
FIG. 1D. Illustration of transgene expression repression mediated by Csy4 endoribonuclease. The model represents a gene-stack composed of Csy4 gene (NLS-Csy4) allowing the expression of the nuclear targeted Csy4 protein and a coding sequence of interest (COI) harboring the DNA sequence corresponding to the Csy4 recognition sequence between the promoter and the encoding region. When both transgenes are expressed, the nuclear-targeted Csy4 cleaves its recognition site located in the 5'UTR (untranslated region) of cogCOI mRNA and removes the 5'UTR including the 5' cap, resulting in translation repression of cogCOI.

Before the invention is described in detail, it is to be understood that, unless otherwise indicated, this invention is not limited to particular sequences, expression vectors, synthetic TF, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature).

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The amino acid sequence of *Pseudomonas aeruginosa* Csy4 is:

```
                                        (SEQ ID NO: 1)
        10         20         30         40
MDHYLDIRLR PDPEFPPAQL MSVLFGKLHQ ALVAQGGDRI 50         60         70         80
GVSFPDLDES RSRLGERLRI HASADDLRAL LARPWLEGLR 90        100        110        120
DHLQFGEPAV VPHPTPYRQV SRVQAKSNPE RLRRRLMRRH 130        140        150        160
DLSEEEARKR IPDTVARALD LPFVTLRSQS TGQHFRLFIR 170        180
HGPLQVTAEE GGFTCYGLSK GGFVPWF
```

An enzymatic active fragment of an endoribonuclease comprises an amino acid sequence having a sequence identity equal to or more than 70%, 80%, 90%, 95%, or 99% to SEQ ID NO:1. In some embodiments, the enzymatic active fragment comprises one or more of the following: H at position 29, E at position 49, R at position 102, Q at position 104, S at position 148, S at position 150, T at position 151, F at position 155, and Y at position 176. In some embodiments, the enzymatic active fragment comprises: H at position 29 and S at position.

The host cell can be an animal or plant cell. The host cell can be a mammalian, insect, or yeast cell. n some embodiments, the vector comprises nucleotide sequences which enable its stable maintenance in the host cell or integration into the genome of the host cell. One skilled in the art is able to determine what sequences to use in a particular host cell. In some embodiments, the host cell is a plant cell, or a plant cell in a plant.

Suitable plant promoters include, but are not limited to, the 35S promoter. The promoter can be heterologous to the gene encoding the endoribonuclease and/or COI.

In some embodiments, the plant is selected from the group consisting of *Arabidopsis*, poplar, *eucalyptus*, rice, corn, switchgrass, sorghum, millet, *miscanthus*, sugarcane, pine, alfalfa, wheat, soy, barley, turfgrass, tobacco, hemp, bamboo, rape, sunflower, willow, and Brachypodium.

In some embodiments, the present invention provides plants, plant cells, seeds, flowers, leave, fruit, or biomass.

Suitable host cells, promoters, nucleotide control sequences, and the like, and techniques thereof, are taught in PCT International Patent Application No. PCT/US2012/023182, which is hereby incorporated by reference.

The invention is useful to engineer plants for biofuel purposes and other uses of biomass as feedstocks for chemical industry. The invention is also useful for engineering of plants, such as crop plants to yield more of one or more certain byproducts. The invention could also be used to increase pathogen resistance or tolerance.

REFERENCES CITED

1. Gonzalez, T. L., Liang, Y., Nguyen, B. N., Staskawicz, B. J., Loqué, D. and Hammond, M. C. (2015) Tight regulation of plant immune responses by combining promoter and suicide exon elements. *Nucleic Acids Res*.
2. Brückner, K., Schafer, P., Weber, E., Grützner, R., Marillonnet, S. and Tissier, A. (2015) A library of synthetic transcription activator-like effector-activated promoters for coordinated orthogonal gene expression in plants. *The Plant Journal*, n/a-n/a.
3. Chern, M., Fitzgerald, H., Canlas, P., Navarre, D. and Ronald, P. (2005) Overexpression of a rice NPR1 homolog leads to constitutive activation of defense response and hypersensitivity to light. *Mol Plant Microbe Interact*, 18, 511-520.
4. Voelker, S. L., Lachenbruch, B., Meinzer, F. C., Jourdes, M., Ki, C., Patten, A. M., Davin, L. B., Lewis, N. G., Tuskan, G. A., Gunter, L. et al. (2010) Antisense down-regulation of 4CL expression alters lignification, tree growth, and saccharification potential of field-grown poplar. *Plant Physiol*, 154, 874-886.
5. Kasuga, M., Liu, Q., Miura, S., Yamaguchi-Shinozaki, K. and Shinozaki, K. (1999) Improving plant drought, salt, and freezing tolerance by gene transfer of a single stress-inducible transcription factor. *Nat Biotech*, 17, 287-291.
6. Hieno, A., Naznin, H. A., Hyakumachi, M., Sakurai, T., Tokizawa, M., Koyama, H., Sato, N., Nishiyama, T., Hasebe, M., Zimmer, A. D. et al. (2014) ppdb: plant promoter database version 3.0. *Nucleic Acids Res*, 42, D1188-1192.
7. Lescot, M., Dehais, P., Thijs, G., Marchal, K., Moreau, Y., Van de Peer, Y., Rouze, P. and Rombauts, S. (2002) PlantCARE, a database of plant cis-acting regulatory elements and a portal to tools for in silico analysis of promoter sequences. *Nucleic Acids Res*, 30, 325-327.
8. Liu, W., Mazarei, M., Peng, Y., Fethe, M. H., Rudis, M. R., Lin, J., Millwood, R. J., Arelli, P. R. and Stewart, C. N., Jr. (2014) Computational discovery of soybean promoter cis-regulatory elements for the construction of soybean cyst nematode-inducible synthetic promoters. *Plant Biotechnol J*, 12, 1015-1026.
9. Bocobza, S. E. and Aharoni, A. (2014) Small molecules that interact with RNA: riboswitch-based gene control and its involvement in metabolic regulation in plants and algae. *Plant J*, 79, 693-703.

10. Moore, I., Samalova, M. and Kurup, S. (2006) Trans-activated and chemically inducible gene expression in plants. *The Plant Journal*, 45, 651-683.
11. Coego, A., Brizuela, E., Castillejo, P., Ruiz, S., Koncz, C., del Pozo, J. C., Pineiro, M., Jarillo, J. A., Paz-Ares, J. and Leon, J. (2014) The TRANSPLANTA collection of *Arabidopsis* lines: a resource for functional analysis of transcription factors based on their conditional overexpression. *Plant J*, 77, 944-953.
12. Wilde, R. J., Shufflebottom, D., Cooke, S., Jasinska, I., Merryweather, A., Beri, R., Brammar, W. J., Bevan, M. and Schuch, W. (1992) Control of gene expression in tobacco cells using a bacterial operator-repressor system. *The EMBO journal*, 11, 1251-1259.
13. Gatz, C., Frohberg, C. and Wendenburg, R. (1992) Stringent repression and homogeneous de-repression by tetracycline of a modified CaMV 35S promoter in intact transgenic tobacco plants. *Plant J*, 2, 397-404.
14. Barkley, M. D. and Bourgeois, S. (1980) In Miller, J. H. and Reznikoff, W. S. (eds.). Cold Spring Harbor Laboratory Press, Cold Spring Harbor, N.Y., pp. 177-220.
15. Bertrand, K. P., Postle, K., Wray Jr, L. V. and Reznikoff, W. S. (1983) Overlapping divergent promoters control expression of Tn10 tetracycline resistance. *Gene*, 23, 149-156.
16. Mahfouz, M. M., Li, L., Piatek, M., Fang, X., Mansour, H., Bangarusamy, D. K. and Zhu, J. K. (2012) Targeted transcriptional repression using a chimeric TALE-SRDX repressor protein. *Plant Mol Biol*, 78, 311-321.
17. Guan, X., Stege, J., Kim, M., Dahmani, Z., Fan, N., Heifetz, P., Barbas, C. F., 3rd and Briggs, S. P. (2002) Heritable endogenous gene regulation in plants with designed polydactyl zinc finger transcription factors. *Proc Natl Acad Sci USA*, 99, 13296-13301.
18. Lowder, L. G., Zhang, D., Baltes, N. J., Paul, J. W., 3rd, Tang, X., Zheng, X., Voytas, D. F., Hsieh, T. F., Zhang, Y. and Qi, Y. (2015) A CRISPR/Cas9 Toolbox for Multiplexed Plant Genome Editing and Transcriptional Regulation. *Plant Physiol*, 169, 971-985.
19. Zhang, B., Pan, X., Cobb, G. P. and Anderson, T. A. (2006) Plant microRNA: A small regulatory molecule with big impact. *Dev. Biol.*, 289, 3-16.
20. Ossowski, S., Schwab, R. and Weigel, D. (2008) Gene silencing in plants using artificial microRNAs and other small RNAs. *Plant J*, 53, 674-690.
21. Zhou, M. and Luo, H. (2013) MicroRNA-mediated gene regulation: potential applications for plant genetic engineering. *Plant Mol Biol*, 83, 59-75.
22. Brown, B. D., Gentner, B., Cantore, A., Colleoni, S., Amendola, M., Zingale, A., Baccarini, A., Lazzari, G., Galli, C. and Naldini, L. (2007) Endogenous microRNA can be broadly exploited to regulate transgene expression according to tissue, lineage and differentiation state. *Nat Biotech*, 25, 1457-1467.
23. Seyhan, A. A. (2016) A multiplexed miRNA and transgene expression platform for simultaneous repression and expression of protein coding sequences. *Molecular bioSystems*, 12, 295-312.
24. Brosnan, C. A. and Voinnet, O. (2011) Cell-to-cell and long-distance siRNA movement in plants: mechanisms and biological implications. *Curr. Opin. Plant Biol.*, 14, 580-587.
25. van Dongen, S., Abreu-Goodger, C. and Enright, A. J. (2008) Detecting microRNA binding and siRNA off-target effects from expression data. *Nat. Methods*, 5, 1023-1025.
26. Cerny, R. E., Qi, Y., Aydt, C. M., Huang, S., Listello, J. J., Fabbri, B. J., Conner, T. W., Crossland, L. and Huang, J. (2003) RNA-binding protein-mediated translational repression of transgene expression in plants. *Plant Mol Biol*, 52, 357-369.
27. Haurwitz, R. E., Jinek, M., Wiedenheft, B., Zhou, K. and Doudna, J. A. (2010) Sequence- and Structure-Specific RNA Processing by a CRISPR Endonuclease. *Science*, 329, 1355-1358.
28. Haurwitz, R. E., Sternberg, S. H. and Doudna, J. A. (2012) Csy4 relies on an unusual catalytic dyad to position and cleave CRISPR RNA.
29. Sternberg, S. H., Haurwitz, R. E. and Doudna, J. A. (2012) Mechanism of substrate selection by a highly specific CRISPR endoribonuclease. *RNA*, 18, 661-672.
30. Qi, L., Haurwitz, R. E., Shao, W., Doudna, J. A. and Arkin, A. P. (2012) RNA processing enables predictable programming of gene expression. *Nat Biotech*, 30, 1002-1006.
31. Du, P., Miao, C., Lou, Q., Wang, Z. and Lou, C. (2015) Engineering Translational Activators with CRISPR-Cas System. ACS Synth Biol.
32. Borchardt, E. K., Vandoros, L. A., Huang, M., Lackey, P. E., Marzluff, W. F. and Asokan, A. (2015) Controlling mRNA stability and translation with the CRISPR endoribonuclease Csy4. *RNA*, 21, 1921-1930.
33. Eudes, A., Sathitsuksanoh, N., Baidoo, E. E., George, A., Liang, Y., Yang, F., Singh, S., Keasling, J. D., Simmons, B. A. and Logue, D. (2015) Expression of a bacterial 3-dehydroshikimate dehydratase reduces lignin content and improves biomass saccharification efficiency. *Plant Biotechnol J*, 13, 1241-1250.
34. Ham, T. S., Dmytriv, Z., Plahar, H., Chen, J., Hillson, N. J. and Keasling, J. D. (2012) Design, implementation and practice of JBEI-ICE: an open source biological part registry platform and tools. *Nucleic Acids Res*, 40, e141.
35. Sparkes, I. A., Runions, J., Kearns, A. and Hawes, C. (2006) Rapid, transient expression of fluorescent fusion proteins in tobacco plants and generation of stably transformed plants. *Nat Protoc.*, 1, 2019-2025.
36. Voinnet, O., Rivas, S., Mestre, P. and Baulcombe, D. (2003) An enhanced transient expression system in plants based on suppression of gene silencing by the p19 protein of tomato bushy stunt virus. *Plant J*, 33, 949-956.
37. Clough, S. J. and Bent, A. F. (1998) Floral dip: a simplified method for *Agrobacterium*-mediated transformation of *Arabidopsis thaliana*. *Plant J*, 16, 735-743.
38. Kanehisa, M., Sato, Y., Kawashima, M., Furumichi, M. and Tanabe, M. (2016) KEGG as a reference resource for gene and protein annotation. *Nucleic Acids Res*, 44, D457-462.
39. Grissa, I., Vergnaud, G. and Pourcel, C. (2007) The CRISPRdb database and tools to display CRISPRs and to generate dictionaries of spacers and repeats. *BMC Bioinformatics*, 8, 172.
40. Chen, S., Tao, L., Zeng, L., Vega-Sanchez, M. E., Umemura, K. and Wang, G.-L. (2006) A highly efficient transient protoplast system for analyzing defence gene expression and protein-protein interactions in rice. *Mol. Plant Pathol.*, 7, 417-427.
41. Visa, N., Izaurralde, E., Ferreira, J., Daneholt, B. and Mattaj, I. W. (1996) A nuclear cap-binding complex binds Balbiani ring pre-mRNA cotranscriptionally and accompanies the ribonucleoprotein particle during nuclear export. *The Journal of Cell Biology*, 133, 5-14.

42. Fuke, H. and Ohno, M. (2008) Role of poly (A) tail as an identity element for mRNA nuclear export. *Nucleic Acids Res.*, 36, 1037-1049.
43. Bell-Lelong, D. A., Cusumano, J. C., Meyer, K. and Chapple, C. (1997) Cinnamate-4-Hydroxylase Expression in *Arabidopsis* (Regulation in Response to Development and the Environment). *Plant Physiol.*, 113, 729-738.
44. Ebert, P. R., Ha, S. B. and An, G. (1987) Identification of an essential upstream element in the nopaline synthase promoter by stable and transient assays. *Proc Natl Acad Sci USA*, 84, 5745-5749.
45. Aoyama, T. and Chua, N. H. (1997) A glucocorticoid-mediated transcriptional induction system in transgenic plants. *Plant J*, 11, 605-612.
46. Padidam, M. (2003) Chemically regulated gene expression in plants. *Curr Opin Plant Biol*, 6, 169-177.
47. Cazzonelli, C. I. and Velten, J. (2006) An in vivo, luciferase-based, *Agrobacterium*-infiltration assay system: implications for post-transcriptional gene silencing. *Planta*, 224, 582-597.
48. Yang, Y., Costa, A., Leonhardt, N., Siegel, R. and Schroeder, J. (2008) Isolation of a strong *Arabidopsis* guard cell promoter and its potential as a research tool. *Plant methods*, 4, 6.
49. Dong, Q., Schlueter, S. D. and Brendel, V. (2004) PlantGDB, plant genome database and analysis tools. *Nucleic Acids Res*, 32, D354-359.
50. Duvick, J., Fu, A., Muppirala, U., Sabharwal, M., Wilkerson, M. D., Lawrence, C. J., Lushbough, C. and Brendel, V. (2008) PlantGDB: a resource for comparative plant genomics. *Nucleic Acids Res.*, 36, D959-D965.
51. Smanski, M. J., Zhou, H., Claesen, J., Shen, B., Fischbach, M. A. and Voigt, C. A. (2016) Synthetic biology to access and expand nature's chemical diversity. *Nat Rev Micro*, 14, 135-149.
52. Liu, W. and Stewart, C. N., Jr. (2015) Plant synthetic biology. *Trends Plant Sci*, 20, 309-317.
53. Jansen, R. P. (2001) mRNA localization: message on the move. *Nat Rev Mol Cell Biol*, 2, 247-256.
54. Murthy, K. G., Park, P. and Manley, J. L. (1991) A nuclear micrococcal-sensitive, ATP-dependent exoribonuclease degrades uncapped but not capped RNA substrates. *Nucleic Acids Res*, 19, 2685-2692.
55. Hugouvieux, V., Murata, Y., Young, J., Kwak, M., Mackesy, D. and Schroeder, J. (2002) Localization, ion channel regulation and genetic interactions during abscisic acid signaling of the nuclear mRNA cap-binding protein, ABH1. *Plant Physiol*, 130, 1276-1287.
56. Hugouvieux, V., Kwak, J. M. and Schroeder, J. I. (2001) An mRNA cap binding protein, ABH1, modulates early abscisic acid signal transduction in *Arabidopsis*. *Cell*, 106, 477-487.
57. Gallie, D. R. (1991) The cap and poly(A) tail function synergistically to regulate mRNA translational efficiency. *Genes Dev*, 5, 2108-2116.
58. Abramson, R. D., Browning, K. S., Dever, T. E., Lawson, T. G., Thach, R. E., Ravel, J. M. and Merrick, W. C. (1988) Initiation factors that bind mRNA. A comparison of mammalian factors with wheat germ factors. *J Biol Chem*, 263, 5462-5467.
59. Frohberg, C., Heins, L. and Gatz, C. (1991) Characterization of the interaction of plant transcription factors using a bacterial repressor protein. *Proceedings of the National Academy of Sciences of the United States of America*, 88, 10470-10474.
60. Weinmann, P., Gossen, M., Hillen, W., Bujard, H. and Gatz, C. (1994) A chimeric transactivator allows tetracycline-responsive gene expression in whole plants. *Plant J*, 5, 559-569.
61. Love, J., Scott, A. C. and Thompson, W. F. (2000) Technical advance: stringent control of transgene expression in *Arabidopsis thaliana* using the Top10 promoter system. *Plant J*, 21, 579-588.
62. Moore, I., Galweiler, L., Grosskopf, D., Schell, J. and Palme, K. (1998) A transcription activation system for regulated gene expression in transgenic plants. *Proc Natl Acad Sci USA*, 95, 376-381.
63. Hickey, S. F., Sridhar, M., Westermann, A. J., Qin, Q., Vijayendra, P., Liou, G. and Hammond, M. C. (2012) Transgene regulation in plants by alternative splicing of a suicide exon. *Nucleic Acids Res.*, 40, 4701-4710.
64. Rose, A. B. (2004) The effect of intron location on intron-mediated enhancement of gene expression in *Arabidopsis*. *Plant J*, 40, 744-751.
65. Meshcheriakova, Y. A., Saxena, P. and Lomonossoff, G. P. (2014) Fine-tuning levels of heterologous gene expression in plants by orthogonal variation of the untranslated regions of a nonreplicating transient expression system. *Plant Biotechnol J*, 12, 718-727.
66. Kanoria, S. and Burma, P. K. (2012) A 28 nt long synthetic 5'UTR (synJ) as an enhancer of transgene expression in dicotyledonous plants. *BMC Biotechnol*, 12, 85.
67. Dugdale, B., Mortimer, C. L., Kato, M., James, T. A., Harding, R. M. and Dale, J. L. (2014) Design and construction of an in-plant activation cassette for transgene expression and recombinant protein production in plants. *Nat. Protocols*, 9, 1010-1027.
68. Mariani, C., De Beuckeleer, M., Truettner, J., Leemans, J., and Goldberg, R. B. (1990). Induction of male sterility in plants by a chimeric ribonuclease gene. *Nature*, 347, 737-741.
69. Singh, S. P., Singh, S. P., Pandey, T., Singh, R. R., and Sawant, S. V. (2015). A novel male sterility-fertility restoration system in plants for hybrid seed production. *Scientific Reports*, 5, 1274.
70. Laubinger, S., Sachsenberg, T., Zeller, G., Busch, W., Lohmann, J. U., Ratsch, G. and Weigel, D. (2008) Dual roles of the nuclear cap-binding complex and SERRATE in pre-mRNA splicing and microRNA processing in *Arabidopsis thaliana*. *Proc Natl Acad Sci USA*, 105, 8795-8800.
71. Nissim, L., Perli, Samuel D., Fridkin, A., Perez-Pinera, P. and Lu, Timothy K. (2014) Multiplexed and Programmable Regulation of Gene Networks with an Integrated RNA and CRISPR/Cas Toolkit in Human Cells. *Mol. Cell*, 54, 698-710.
72. Patron, N. J., Orzaez, D., Marillonnet, S., Warzecha, H., Matthewman, C., Youles, M., Raitskin, O., Leveau, A., Farre, G., Rogers, C. et al. (2015) Standards for plant synthetic biology: a common syntax for exchange of DNA parts. *The New phytol.* 208, 13-19.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Endoribonuclease-Based Two-Component Repressor Systems for Tight Expression Control in Plants Tight control and multifactorial regulation of gene expression are important challenges in genetic engineering and are critical for the development of regulatory circuits. In synthetic biology, meeting these challenges will facilitate targeted gene expression and the fine-tuning of metabolic pathways to avoid the accumulation of undesired intermediates that would be toxic in some cells. By employing the endoribonuclease Csy4 and its recognition sequence from the CRISPR/Cas system in *Pseudomonas aeruginosa* and manipulating 5'UTR of mRNA, we developed a two-component expression-repression system to tightly control synthesis of transgene products. We demonstrated this regulatory device was functional in monocotyledonous and dicotyledonous species, and showed that it can be used to repress transgene expression by >400-fold and to synchronize repression of multiple transgenes. Moreover, we validated this system's capacity to offer not only tissue-specific transgene repression, but also stimuli-dependent expression control. Finally, using a bioinformatics approach, we identified 54 orthologous systems from various bacteria, and then validated in planta the activity for three out of six of those systems, demonstrating the potential diversity of such two-component repressor system.

Here we present the design of a two-component expression-repressor system to support tight control of transgene expression in plants. We use the site-specific endoribonuclease (endoRNase) Csy4—the CRISPR/Cas Subtype Ypest protein 4 from CRISPR/Cas system in *Pseudomonas aeruginosa* (27). Csy4 is a small protein of 187-amino-acids with a molecular weight of 21 kD that cleaves a 28-nucleotide sequence originally found within the repetitive units of the precursor CRISPR RNA (27). Csy4's small size, high fidelity, and known recognition sequence have attracted interest for its use as a major component in several synthetic devices (27-29). In *E. coli*, Csy4 and its recognition sequence were used to control the integrity of mRNA regulatory elements and enabled predictable regulation of multi-gene operons (30). Qi et al. also showed that Csy4 could be used to repress expression of chimeric GFP in *Saccharomyces cerevisiae* when the coding sequence was truncated after the cleavage of Csy4's recognition sequence (30). Most recently in *E. coli*, Csy4's recognition sequence was used to control the removal of a cis-repressive RNA module that acts as translational repressor. The elimination of the repressor element upon Csy4 expression was used to relieve translation inhibition (31). Activity and kinetics of Csy4 for transgene mRNA cleavage have also been studied in mammalian cells (32).

In this study, we showed that Csy4 can be used to repress transgene expression by >400-fold and to synchronize repression of multiple transgenes. It is also a versatile tool for depleting transgene products in a cell-type-specific manner and after the perception of an external stimulus. We demonstrated for three reporter proteins that their expression is effectively repressed by Csy4 activity on their respective mRNA, without modifying their original encoding sequences. Moreover, we isolated several Csy4 orthologous systems and validated the activity for three of them. Finally we showed that Csy4 was effective in repressing transgene expression in at least three plant species—including dicotyledonous and monocotyledonous plants suggesting that this approach could be deployed to control a large diversity of transgenes in various host plants.

Materials and Methods

Construction of Multi-Gene Plasmids

Construction of multi-gene plasmids was carried out using the MultiSite Gateway 3-fragment reaction (MultiSite Gateway® Pro, Invitrogen). Briefly, the Gateway reaction allows building a transgene cluster of Promoter1::Gene1::Terminator1-Promoter2::Gene2::Terminator2 in a binary vector. The destination vector for the Gateway reaction is a binary vector with plant Promoter1 located upstream of the attR1 recombination site and Terminator2 located downstream of attR2 recombination site. The three types of entry clones used correspond to attL1-Gene1-attL4, attR4-Terminator1-Promoter2-attR3, attL3-Gene2-attL2, respectively. Each MultiSite Gateway reaction was performed with the LR Clonase™ II Plus enzyme mix and equal molar of each component construct according to the manufacturer's manual. More details about the destination vector and the entry clones are described below. A list of expression clones, the destination vectors and entry clones is presented in Table 1. Cloning primers are listed in Table 2.

Most of the destination vectors are a series of vectors developed based on pTKan-p35S::attR1-GW-attR2::tRBCS (1). pTKan-pAct2::cogRFP::tNOS-p35S::attR1-GW-attR2::tRBCS was assembled using an in-fusion cloning kit (In-Fusion® HD, Clontech) by incorporation of PCR fragments of pAct2 and cogRFP-tNOS at the ApaI site located between the T-DNA Right Border and p35S promoter of the pTKan-p35S::attR1-GW-attR2::tRBCS vector. The pTKan-p35S::RFP::tNOS-p35S::attR1-GW-attR2::tRBCS and the pTKan-pNOS::RFP::tNOS-p35S::GVG::tE9-pUAS::attR1-GW-attR2::tRBCS vectors were constructed as described in Gonzalez, Liang et al. 2015. The pTKan-p35S::attR1-GW-attR2::YFP::tRBCS vector was provided by Eudes et al. (33).

Genes of interest were synthesized (GenScript, Piscataway, N.J., USA) or PCR amplified with attB sites incorporated. BP recombination reactions (MultiSite Gateway® Pro, Invitrogen) were performed with each gene of interest and pDONR221 P1-P4 or pDONR221 P3-P2 vectors to generate entry clones corresponding to attL1-Gene1-attL4 or attL3-Gene2-attL2, respectively. Entry clones encoding attR4-Terminator1-Promoter2-attR3 were developed based on pDONR221-attR4-tG7-pC4H-attR3, in which the pC4H fragment was removed using both AvrII and HindIII restriction enzymes and replaced by PCR products corresponding to pNOS, pGCI or pZmUbi inserted by in-fusion cloning (In-Fusion® HD, Clontech). All sequences and plasmids developed under this project will be made publicly available through the ICE repository (34)

*Agrobacterium*-Mediated Transient Leaf Transformations

Binary vectors based on the pTKan plasmid were transformed into *Agrobacterium tumefaciens* strain GV3101 and selected on LB plates containing 100 μg/mL rifampicin, 30 μg/mL gentamicin and 50 μg/mL spectinomycin. *Agrobacterium*-mediated transient leaf transformation was performed as described previously (35) with small modifications. Briefly, 5 mL *agrobacterium* liquid culture was grown for 20 to 24 h at 30° C. *Agrobacterium* cells were pelleted by centrifugation at 5,000 g for 5 min and resuspended in infiltration medium, containing 50 mM MES-KOH, pH 5.6, 2 mM $Na_3PO_4$, 0.5% (w/v) dextrose and 200 μM acetosyringone. *A. tumefaciens* strain C58C1 containing p19 plasmid (36) was selected on LB plates containing 100 μg/mL rifampicin, 5 μg/mL tetracycline and 50 μg/mL kanamycin and cultured under the same condition as strain GV3101. Both *Agrobacterium* strains were adjusted to a final $OD_{600\ nm}$ 0.3 before co-infiltration to *Nicotiana benthamiana* leaves with a needleless syringe. *N. benthamiana* plants were grown in a growth chamber under 16/8 h and 26/24° C. day/night cycles. Three-to-four week old plants were used for leaf infiltration.

Whole Leaf Imaging for Fluorescent Signals

Three days after infiltration, tobacco leaves were detached from the plants and imaged for fluorescence signals with an Amersham Imager 600 (GE Healthcare Life Sciences). GFP and RFP epi-fluorescence signals were detected and imaged with the preset blue light settings (excitation 460 nm, Cy2:525BP20 filter) and green light settings (excitation 520 nm, Cy3:605BP40 filter), respectively. Time needed for signal saturation for the strongest signal intensity in the image was set as the exposure time for imaging.

RT-PCR and Real-Time qPCR Analysis

For RNA extraction, 50 to 100 mg leaf samples were snap frozen in liquid nitrogen after fluorescence analysis until further analysis. RNA isolation and purification was performed using the RNeasy Plant Mini Kit (Qiagen) and the RNase-Free DNase Set (Qiagen). 400 to 1000 ng of total RNA was used for cDNA synthesis using the Transcriptor High Fidelity cDNA Synthesis Kit (Roche). Absence of DNA contamination in the RNA samples was confirmed each time by the absence of amplification of ELONGATION FACTOR 1 in the negative control samples that were generated for each RNA sample by excluding reverse-transcriptase in the cDNA synthesis reaction. RT-PCR was performed using OneTaq DNA polymerase (New England Biolabs, Ipswich, Mass., USA) and gene-specific primers (Table 2). The number of amplification cycles was adjusted for each gene to avoid reaching reaction saturation. For real-time qPCR analysis, cDNAs were amplified using the QuantiFast SYBR Green PCR kit (Qiagen) in the CFX96 Real-Time System (BIO-RAD). The multi-gene expression binary vectors harbor a kanamycin-resistant marker (Kan) under the control of the manopine synthase promoter (pMAS) for plant selection. The expression of the Kan gene was used as the reference gene for normalization for qPCR analysis. Primer sequences for RT-PCR and real-time qPCR analysis are listed in Table 2.

Activity Detection of Firefly Luciferase

For activity detection of firefly luciferase in tobacco leaves, leaf discs were made using a cork borer (Cole-Parmer) from tobacco leaves two days after infiltration. Leaf discs from similar locations on each side of a leaf were used for comparison between treatments with or without DEX induction. Incubation media were composed of tobacco Infiltration Media supplemented with 1 mM D-Luciferin (Thermo Fisher Scientific Inc.), 0.5% (v/v) DMSO and 15 μM DEX. DEX was omitted for non-DEX treatments. Chemiluminescent images were taken in manual mode for 5 min with an Amersham Imager 600 (GE Healthcare Life Sciences).

*Arabidopsis* Plant Growth and Transformation

Wild type and transgenic *A. thaliana* plants in the study were of Col-0 ecotype. Plant growth conditions were 16/8 h day/night cycles, 23° C. and 60% humidity. *Agrobacterium* strain GV3101 harboring the desired binary vectors was used to transform *Arabidopsis* plants with the floral dip method (37). T1 and T2 transgenic plants were selected on Murashige and Skoog medium (PhytoTechnology Laboratories, Shawnee Mission, Kans.) supplemented with 1% sucrose, 0.8% (w/v) agar and 50 μg/mL kanamycin.

Identification of CSY4 Orthologs

Three KEGG (38) orthologous groups were identified as CRISPR-associated endoribonucleases: K19091, K19126, and K19130 (http://www.genome.jp/kegg/ko.html). Each enzyme in these three groups was compared to each other for unique protein sequence so that no duplicates would be screened. The genome containing each unique Cas enzyme was then scanned with CRISPRdb (39) for the associated CRISPR repeat sequence (http://crispr.u-psud.fr/crispr/). Any enzyme that existed in a genome with more than one CRISPR repeat sequence was discarded. Enzymes with the same recognition sequence as other enzymes were discarded so that no duplicates would be screened. The growth requirements of the hosting organisms were then examined; we discarded all enzymes whose native host preferred growth below 10° C. or above 37° C. to better match the mesophilic environment the enzymes would encounter in plant cells. The filtered orthologs were clustered by a multiple sequence alignment of their recognition repeats and a single representative of each clade was nominated for BLASTing and synthesis.

Transcript BLAST in Plant GDB

BLAST searches for recognition sequences of Csy4 and its orthologs were performed at the PlantGDB BLAST website (http://www.plantgdb.org/cgi-bin/blast/PlantGDB-blast). The BLAST was performed against sequences in mRNA databases (EST, cDNA, HTC, TSA, EST) for all plant species present in Plant GDB. Default searching parameters were applied.

Rice Protoplast Isolation and Transformation

Seeds of *Japonica* rice Cv. Kitaake were surface sterilized with 95% ethanol for 1 min, 50% bleach for 20 min and washed extensively before growth on solid medium containing half Murashige and Skoog medium (PhytoTechnology Laboratories, Shawnee Mission, Kans.), 3% sucrose, and 0.15% (w/v) phytagel. Rice seedlings were grown in dark conditions for 10 to 15 days. Shoot parts were then harvested for protoplast isolation and transformation as described by Chen et al. (40)

Microscopy

An LSM 710 confocal Microscope (Carl Zeiss) was used for confocal laser-scanning microscopy of tobacco and *Arabidopsis* leaf epidermal cells. The excitation and detection wavelengths were as follows: excitation 488 nm, emission 500-540 nm for GFP; excitation 553 nm, emission 580-650 nm for RFP; and excitation 514 nm, emission 520-620 nm for YFP. Images were processed using the Zeiss LSM Image Browser and Adobe Photoshop CS6.

Fluorescence of rice protoplast cells was visualized using an epifluorescence microscope (Leica DM4000B). GFP fluorescence detection was performed with a 350-680 nm LED light source (SOLA SM II 365, Lumencor), and a GFP filter cube (excitation filter 470BP40 nm; dichromatic mirror 500 nm; suppression filter 525BP50 nm). Images were captured using MetaMorph software and processed with Adobe Photoshop CS6.

Results

Csy4 Represses cogGFP and cogRFP Expression in Tobacco Leaves

Figure 9:
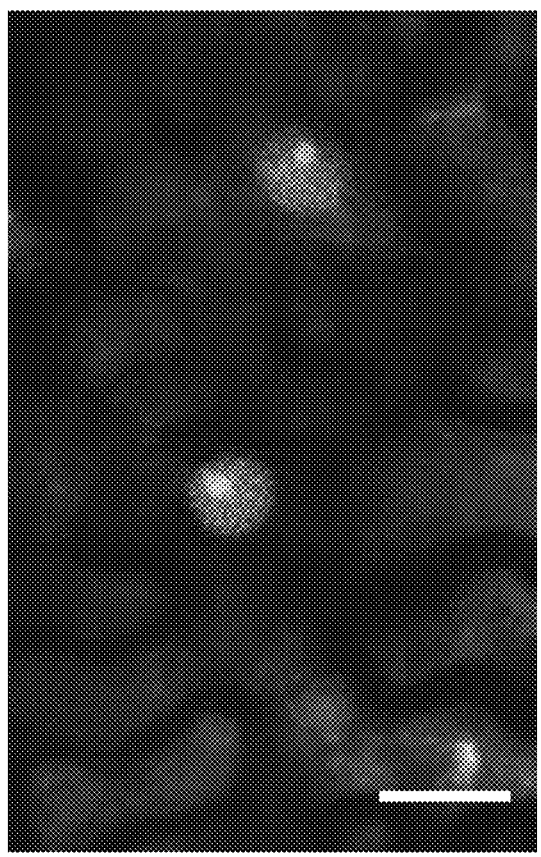
FIG. 9. Visualization of Csy4 targeted to nucleus. A Csy4::YFP construct encoding sequence of Csy4 with an N-terminal nuclear localization signal and a C-terminal YFP fusion under the control of the p35S promoter was transiently expressed in tobacco leaves. Confocal imaging of leaf epidermis was performed at 514 nm excitation with a 520-620 nm emission filter for YFP detection. Scale bar: 20 µm.

A plant codon optimized DNA sequence encoding a fusion protein corresponding to a nuclear localization signal (NLS) linked to Csy4 from *P. aeruginosa* was generated to test the endoRNase activity of Csy4 in plants. The used of the NLS allows targeting Csy4 protein to nucleus in order to minimize the export of Csy4-cleaved mRNA since untranslated regions (UTRs) are important elements contributing to nuclear mRNA export (41,42). Nuclear localization of the synthetic Csy4 was confirmed when YFP was fused to its C-terminus (FIG. 9). Reporter genes (cogGFP or cogRFP) were constructed by inserting the recognition sequence of Csy4 in the 5'UTR, right before the start codon of the GFP or RFP coding-region, such that the 5'UTR—including mRNA cap—would be removed after cleavage. Our hypothesis is that Csy4 cleavage could simultaneously destabilize, reduce nuclear export, and inhibit translation of target transcripts; and thus abolish transcript expression (FIG. 1A to 1D). For each experiment, all genes were stacked in a single T-DNA to enable co-delivery and genomic co-localization of Csy4 and reporter genes into transgenic cells or plants. In the control constructs, the encoding sequence of the hygromycin-resistance (HPTII) protein was used to replace that of the nuclear-targeted Csy4 protein.

Figure 2A:
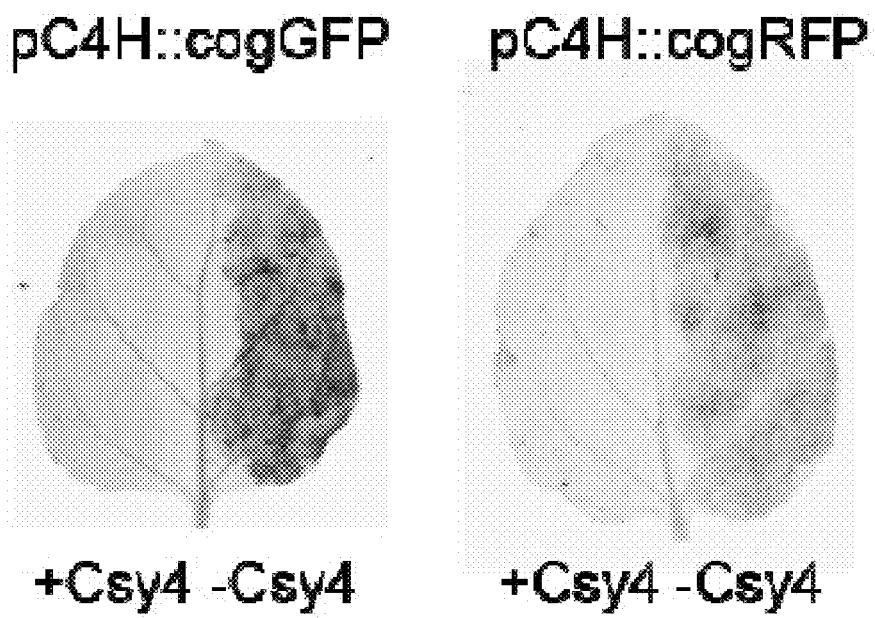
FIG. 2A. Csy4 dependent repression of cogGFP and cogRFP in tobacco leaves. The structure of the transgene cassette was shown in FIG. 1D, where cogCOI is replaced by cogGFP (or cogRFP). The "+Csy4" DNA stack contains the cogGFP (or cogRFP) and the Csy4 gene that is controlled by the 35S promoter while in the "−Csy4" DNA stack, the encoding sequence of Csy4 was replaced by that of HPTII. The Arabidopsis C4H promoter was used to express cogGFP (or cogRFP) gene in two sets of experiments, respectively. Fluorescence imaging of whole leaves was performed at 460 nm excitation with a 525BP20 emission filter for GFP detection; and at 520 nm excitation with a 605BP40 emission filter for RFP detection.
Figure 2B:
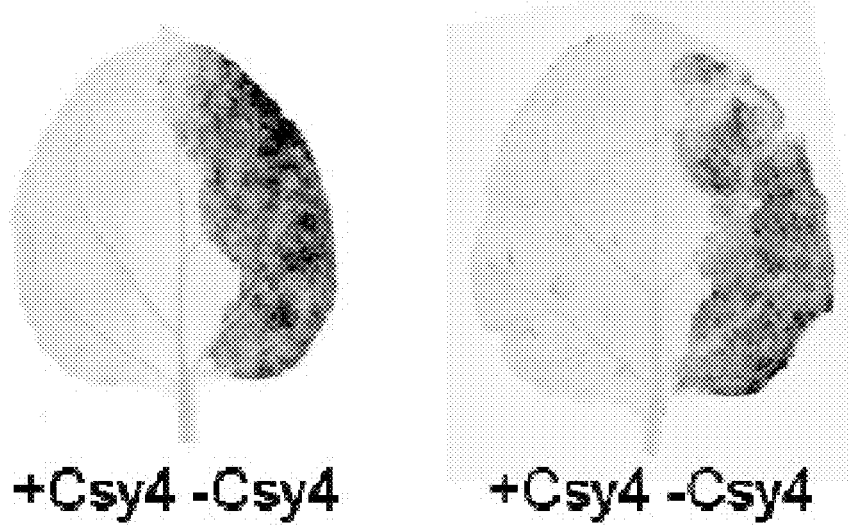
FIG. 2B. Csy4 dependent repression of cogGFP and cogRFP in tobacco leaves. The structure of the transgene cassette was shown in FIG. 1D, where cogCOI is replaced by cogGFP (or cogRFP). The "+Csy4" DNA stack contains the cogGFP (or cogRFP) and the Csy4 gene that is controlled by the 35S promoter while in the "−Csy4" DNA stack, the encoding sequence of Csy4 was replaced by that of HPTII. The Arabidopsis NOS promoter was used to express cogGFP (or cogRFP) gene in two sets of experiments, respectively. Fluorescence imaging of whole leaves was performed at 460 nm excitation with a 525BP20 emission filter for GFP detection; and at 520 nm excitation with a 605BP40 emission filter for RFP detection.

We first tested and confirmed that the insertion of the recognition sequence of Csy4 per se does not affect transgene expression, and did so by comparing fluorescent signals in pC4H::GFP versus pC4H::cogGFP, and pC4H::RFP versus pC4H::cogRFP via transient expression assays in tobacco leaves (data not shown). Then, constructs p35S::Csy4+pC4H::cogGFP and p35S::HPTII+pC4H::cogGFP were agro-infiltrated into each half of the same tobacco leaf for expression assays. GFP fluorescence was detected in the absence of Csy4 but lost in its presence (FIG. 2A and FIG. 2B). Similar results were obtained for RFP fluorescence when the p35S::Csy4+pC4H::cogRFP and p35S::HPTII+pC4H::cogRFP construct pair were used (FIG. 2A and FIG. 2B). pC4H is the promoter region of *Arabidopsis* cinnamate-4-hydroxylase, which is expressed in both vascular tissues and epidermal tissues in *Arabidopsis* (43). To achieve higher expression strength of the reporter genes, pC4H was replaced by a constitutive promoter corresponding to that of the nopaline synthase gene (pNOS; (44)), in the second set of experiments. The results showed that the GFP or RFP fluorescence derived from the expression of pNOS::cogGFP or pNOS::cogRFP, respectively, was efficiently reduced in the presence of p35S::Csy4—suggesting an efficient translation repression of both cogGFP and cogRFP mRNA (FIG. 2A and FIG. 2B).

Csy4 Represses cogGFP and cogRFP Expression Through Transcript Cleavage

Figure 3A:
FIG. 3A. Csy4 cleavage activity on cogGFP and cogRFP. Illustration of cogCOI transcript showing the positions of the primers used for RT-PCR analysis. S cog, the primer pair spanned Csy4 recognition site. D cog, the primer pair located at the 3' end of the mRNA (the distal downstream of the Csy4 recognition site).
Figure 3B:
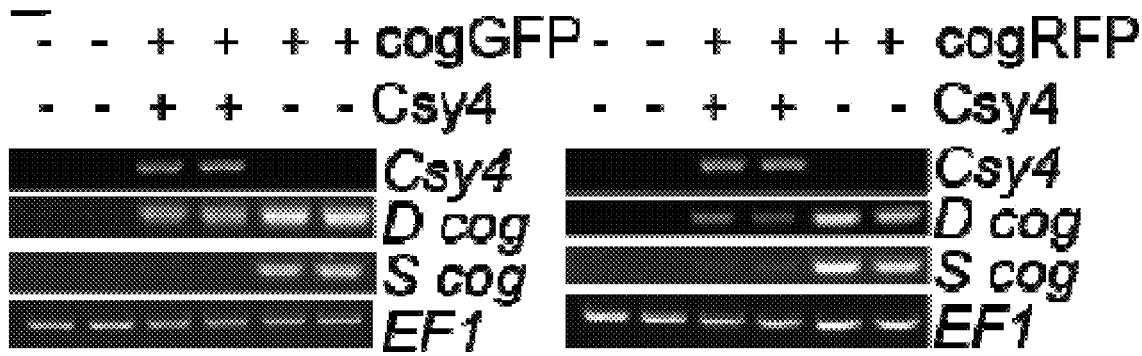
FIG. 3B. Csy4 cleavage activity on cogGFP and cogRFP. Semi-quantitative RT-PCR analysis of cogGFP (or cogRFP) transcript in the presence or absence of Csy4 expression. Tobacco ELONGATION FACTOR 1 (EF1) was used as the reference gene.

To confirm that the elimination of fluorescence from the reporter genes is due to mRNA cleavage mediated by Csy4, primers located either spanning or distal to the downstream side of the Csy4 recognition site were utilized for RT-PCR to analyze the levels and integrity of reporter gene transcripts (FIG. 3B). With the primers spanning the recognition site, strong amplification was obtained in tissues when Csy4 was not expressed, while no or residual amplification was detected in samples in which Csy4 was co-expressed. In contrast, primers located distal to the recognition site (near the 3'UTR) detected significant amount of cogGFP and cogRFP transcripts, although at a reduced level in Csy4-expressing tissues compared to those in the control tissues.

Figure 3C:
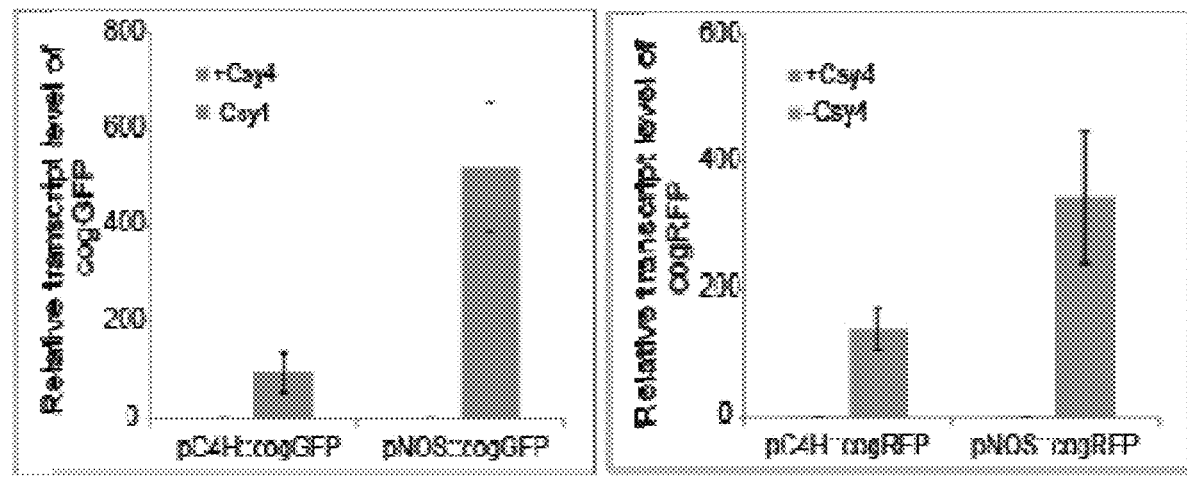
FIG. 3C. Csy4 cleavage activity on cogGFP and cogRFP. Real-time qPCR analysis for the fold change of cogGFP (or cogRFP) transcript in the presence or absence of Csy4 expression. Expression of Kanamycin resistance gene present on the T-DNA was used as the reference gene to calculate the relative abundance of intact cogGFP (or cogRFP) mRNA (non-cleaved mRNA). Blue bars represent the relative abundance of intact cogGFP (or cogRFP) transcript in the presence of Csy4. Green and orange bars represent the relative abundance of intact cogGFP and cogRFP transcripts respectively in the absence of Csy4.

Real-time qPCR was performed to quantify the cleavage efficiency of Csy4 via magnitude of the transcript reduction of the reporter genes in the presence or absence of Csy4 (FIG. 3C). Primers spanning the Csy4 recognition site were used for quantifying the amount of intact reporter gene transcripts. With pC4H driving the reporter genes, Csy4 expression leads to an approximately 90- and 100-fold reduction in cogGFP and cogRFP transcript levels, respectively. With the strong NOS promoter driving the expression of the reporter genes, Csy4 expression leads to an approximately 500- and 400-fold reduction in cogGFP and cogRFP transcript levels, respectively.

Csy4 Allows Synchronized Repression of cogGFP and cogRFP

Figure 4:
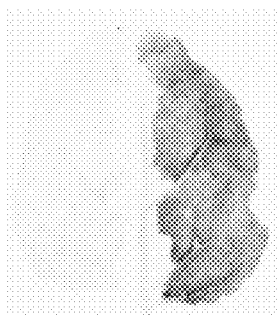
FIG. 4. Csy4 simultaneous repression of cogRFP and cogGFP. Representative GFP and RFP fluorescence images of a leaf infiltrated with Agrobacterium harboring a T-DNA containing cogRFP, cogGFP and Csy4 (+Csy4; left side of the leaf), or cogRFP, cogGFP and HPTII (−Csy4; right side of the leaf). Constitutive promoters, the Arabidopsis ACTIN2 promoter (pAct2), the 35S promoter (p35S) and the NOS promoter (pNOS) were used to express cogRFP, cogGFP and Csy4 or HPTII, respectively. Fluorescence imaging of whole leaves was performed at 460 nm excitation with a 525BP20 emission filter for GFP detection; and at 520 nm excitation with a 605BP40 emission filter for RFP detection.
Figure 4:
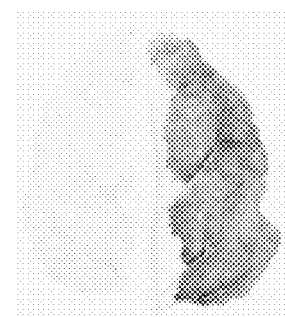

After demonstrating that Csy4 can effectively repress protein accumulation from one transgene, we further investigated the capacity of Csy4 to simultaneously control the expression of multiple genes and generated a multi-gene expression cassette containing the following genes: pAct2::cogRFP, p35S::cogGFP, and pNOS::Csy4. We also generated an expression control cassette in which the encoding sequence of HPTII was used to replace that of Csy4. Fluorescence analysis of GFP and RFP showed that both were deeply reduced in tissues transformed with the gene cassette harboring the Csy4 gene, indicating that Csy4 was capable of synchronizing expression repression of both transgenes (FIG. 4).

Csy4 Allows Conditional Repression of cogFLUC

Figure 5:
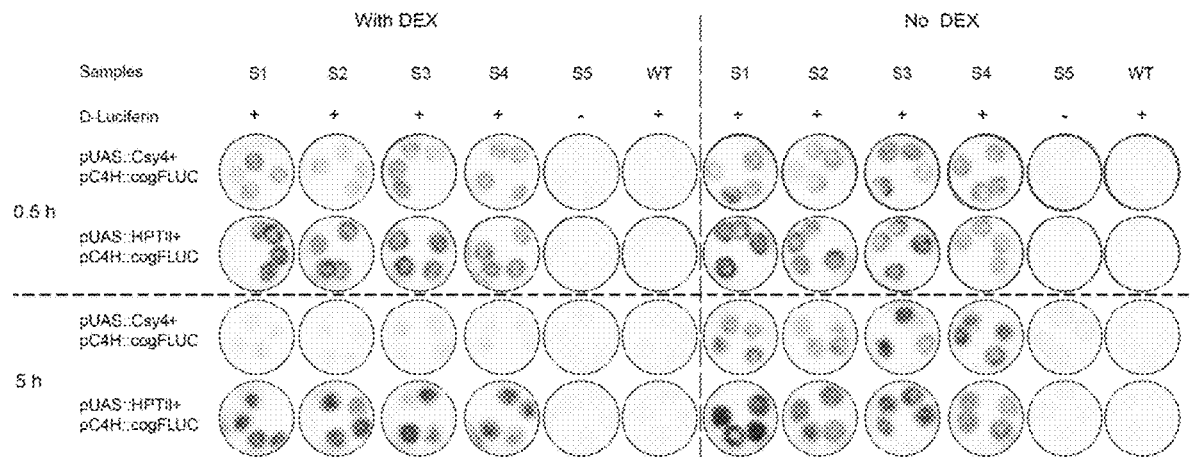
FIG. 5. Inducible repression of cogFLUC mediated by Csy4 in tobacco leaves. Tobacco leaves were infiltrated with Agrobacterium harboring a T-DNA containing a firefly luciferase gene with Csy4 recognition sequence (cogFLUC) under the control of the Arabidopsis C4H promoter (pC4H) and Csy4 (pUAS::Csy4+pC4H::cogFLUC) or HPTII (pUAS::HPTII+pC4H::cogFLUC) genes under the control of dexamethasone (DEX) inducible promoter (pUAS). Leaf discs were excised from infiltrated tobacco leaves two days after infiltration and immersed in reaction media containing no (−; sample S5) or 1 mM D-luciferin substrate (+; samples S1 to S4 and WT) and 0.5% (v/v) DMSO with (With DEX) or without (No DEX) 15 μM DEX. Chemiluminescence images of the samples treated for 0.5 and 5 h were shown.

The use of conditionally active promoters to drive the expression of Csy4 would permit the repression of transgene expression under specific stimuli. Therefore we picked the widely used dexamethasone (DEX) induction system (45, 46) to control the expression of Csy4 and test whether we could conditionally repress transgene expression after a stimulus (supply of DEX for this promoter). A multi-gene expression cassette was built containing p35S::GVG synthetic transcription factor, pUASx6::Csy4 and pC4H::cogFireflyLuciferase (cogFLUC); and a control cassette was generated by replacing Csy4 encoding sequence by that of HPTII. Leaf discs were cut from the same agro-infiltrated leaves and split into two sample sets for treatments with or without the DEX inducer. Regardless of DEX content, the reaction media contained D-luciferin, the substrate for FLUC, and DMSO, to increase the accessibility of D-luciferin to cells (47). Chemiluminescence imaging of leaf discs were taken 10 min, 30 min, 1 h, 3 h, and 5 h after transfer of the samples in the reaction media. When leaf discs were immersed in the luciferin solution containing DEX, luminescent signal from leaves agro-infiltrated with the construct harboring pUASx6::Csy4 peaked at 0.5 h and started to decay around 1 h after the beginning of the treatment. After 5 h, the luminescent signal almost completely disappeared, showing that there was no new FLUC protein synthesized (FIG. 5). When leaf discs were immersed in the luciferin solution without the DEX inducer, luminescent signal from leaves transformed with the cassette containing pUASx6::Csy4 showed no significant luminescence changes between 0.5 to 5 h. The luminescent signal from leaves agro-infiltrated with the control cassette containing pUASx6::HPTII instead of pUASx6::Csy4 showed no significant luminescence changes regardless of the presence of DEX inducer. All taken together, these findings show that the DEX inducer was necessary to induce Csy4 expression to repress FLUC protein synthesis, and thus FLUC-dependent luminescence.

Csy4 can be Used for Cell-Type-Specific Repression of cogGFP

Figure 6:
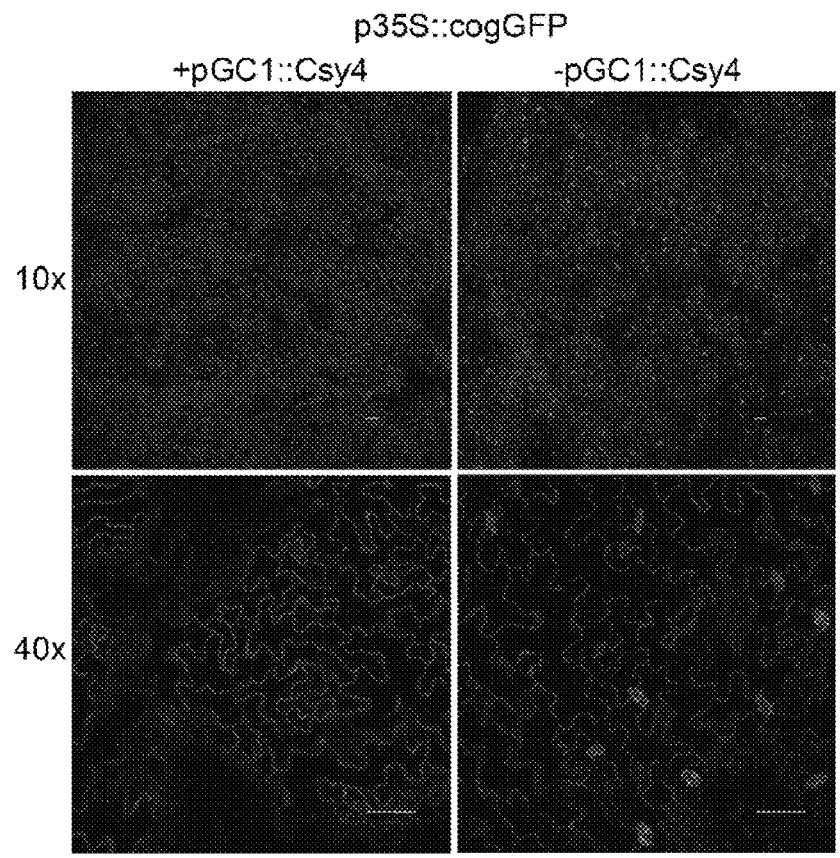
FIG. 6. Use of Csy4 to specifically repress cogGFP expression in guard cells. Representative GFP fluorescence image of leaf epidermis from Arabidopsis lines harboring a T-DNA composed of cogGFP gene under the control of the p35S promoter (p35S::cogGFP) and Csy4 gene under the control of the Arabidopsis guard cell specific promoter (+pGC1::Csy4) or HPTII gene instead of Csy4 gene (−pGC1::Csy4). Confocal imaging of leaf epidermis was performed at 488 nm excitation with a 500-540 emission filter for GFP detection. Scale bar: 50 μm.

The use of developmentally regulated or tissue-specific promoters to drive the expression of Csy4 would permit the repression of transgene expression or eliminate transgene product(s) in a spatiotemporal manner. Thus we selected a guard-cell-specific promoter pGC1 (48) to control the expression of Csy4 and test whether we could repress transgene expression only in guard cells. Stably transformed *Arabidopsis* plants harboring a gene cassette consisting of p35S::cogGFP, pNOS::cogRFP, and Csy4 driven by pGC1 were generated, as were control *Arabidopsis* lines harboring the same gene cassette except that the encoding sequence of Csy4 was replaced by that of HPTII. Fluorescence analysis of the control lines shows that GFP expression was seen in all epidermal cells, including guard cells (FIG. 6). In contrast, GFP signal was significantly reduced or absent in the guard cells of T1 *Arabidopsis* lines containing the pGC1:: Csy4 gene (FIG. 6). These results not only indicate that Csy4 is active in stable transgenic lines but also show that Csy4 can be applied to repress transgene expression in a cell-type-specific manner. cogRFP expression was observed in epidermal cells except in guard cells of all the lines (controls and those harboring pGC1::Csy4 gene; data not shown). It is most likely that pNOS is either not active, or very poorly active, in guard cells.

Csy4 Expression does not Affect Plant Growth

Figure 10A:
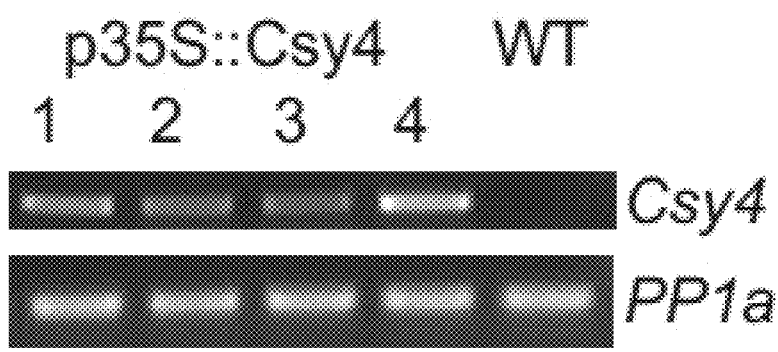
FIG. 10A. Phenotypic analysis of Arabidopsis plants transformed with p35S::Csy4 at different developmental stages. Expression analysis of Csy4 in leaves of four independent transgenic lines by semi-quantitative RT-PCR. The Arabidopsis PPIa gene was used as the reference gene and for quality control in the RT-PCR analysis.
Figure 10B:
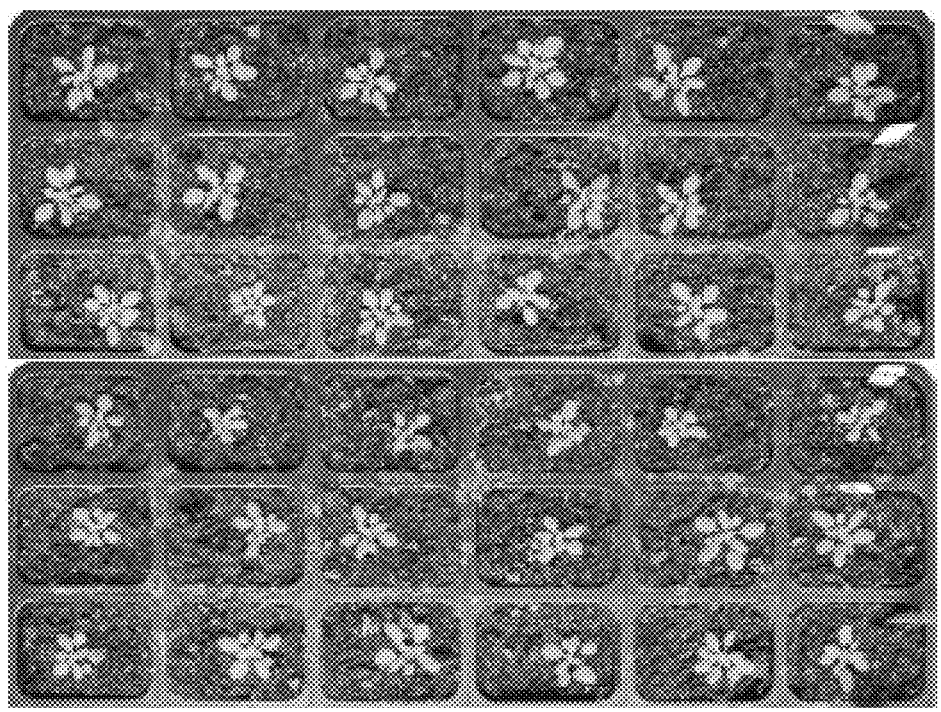
FIG. 10B. Phenotypic analysis of Arabidopsis plants transformed with p35S::Csy4 at different developmental stages. Whole plant image of four independent p35S::Csy4 transgenic lines (Line 1, 2, 3 and 4) and one control line (WT) at 20 days post-germination is shown.
Figure 10C:
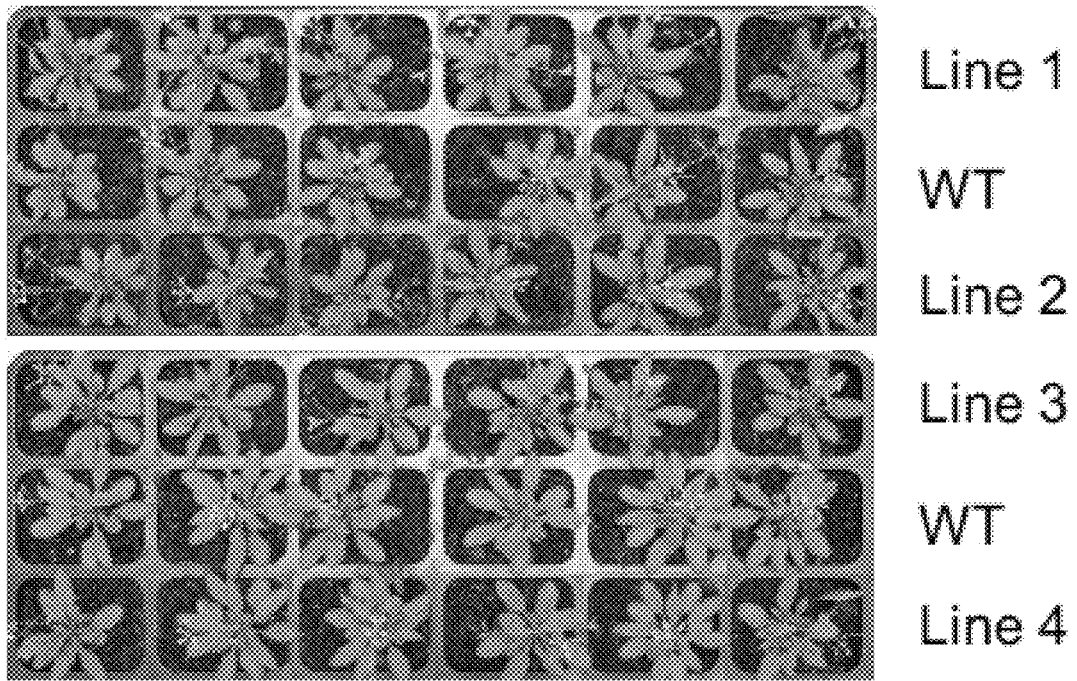
FIG. 10C. Phenotypic analysis of Arabidopsis plants transformed with p35S::Csy4 at different developmental stages. Whole plant image of four independent p35S::Csy4 transgenic lines (Line 1, 2, 3 and 4) and one control line (WT) at 32 days post-germination is shown.
Figure 10D:
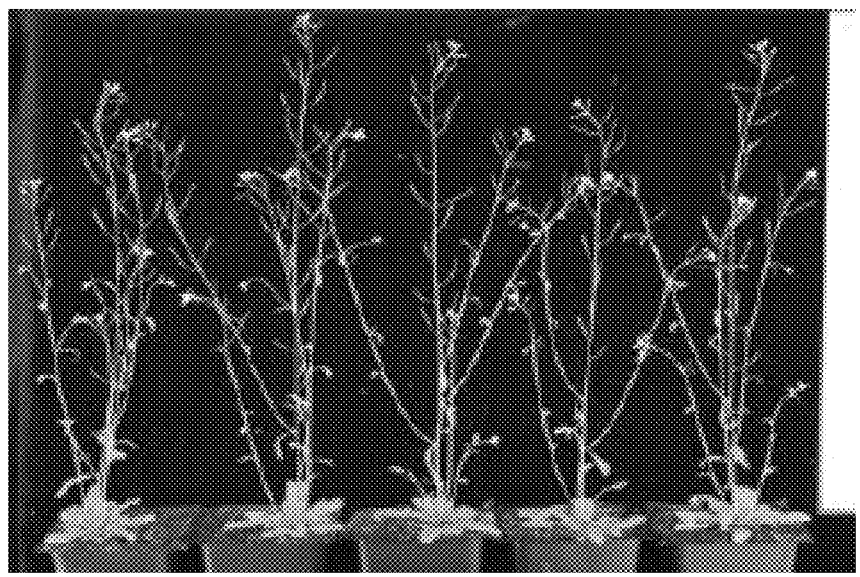
FIG. 10D. Phenotypic analysis of Arabidopsis plants transformed with p35S::Csy4 at different developmental stages. Whole plant image of four independent p35S::Csy4 transgenic lines (Line 1, 2, 3 and 4) and one control line (WT) at 41 days post-germination is shown.

The application of a heterologous or synthetic regulatory system in plants has a prerequisite that the expression of the regulator should not interrupt normal plant growth and development. When Csy4 was driven by a cell-type-specific promoter, pGC1::Csy4, transgenic *Arabidopsis* lines did not show abnormal phenotypes (data not shown). We further generated *Arabidopsis* transgenic lines carrying the p35S:: Csy4 gene, which constitutively expresses Csy4. Expression of Csy4 in leaves of T2 transgenic lines were confirmed by RT-PCR (FIG. 10A). The T2 p35S::Csy4 lines did not show abnormal phenotypes compared to wild type plants at all checked growth stages (FIG. 10B-D).

Specificity of Csy4 cutting activity to its recognition sequence has been tested and proven in bacteria (27). The recognition sequence of Csy4 was BLASTed against the Plant Genome Database (Plant GDB) (http://www.plantgdb.org/cgi-bin/blast/PlantGDBblast), which uploads sequence data from GenBank and UniProt and stores data after reorganization, curation, and processing (49). A non-redundant set of PlantGDB-assembled Unique Transcripts (PUTs) is assembled by Plant GDB for all species with >10,000 published transcripts (50). Transcript BLAST in Plant GDB searches for homologous sequences from transcript-related databases of GenBank as well as from PUTs. Four entries containing the Csy4 recognition sequence were identified but correspond to a single cDNA sequence (gi 189453176) from *Papaver somniferum*. None was found in the other plant species.

Csy4 Represses cogGFP Expression in Rice Protoplast

Figure 7:
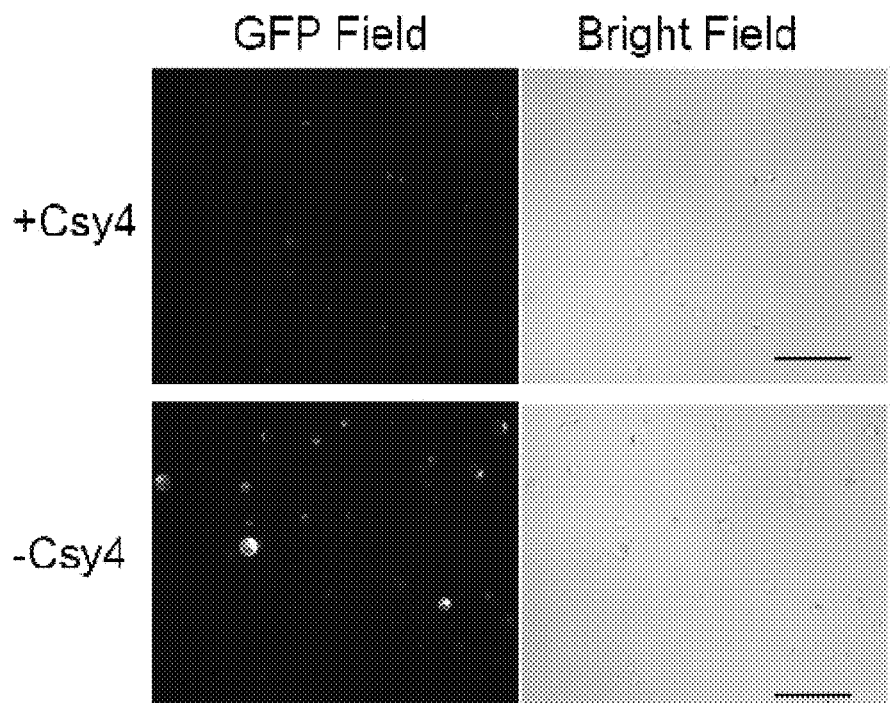
FIG. 7. Csy4-dependent repression of cogGFP in rice protoplasts. Representative GFP fluorescence image (GFP Field) of rice protoplasts transformed with a plasmid harboring a cogGFP gene under the control of the Arabidopsis C4H promoter and the Csy4 gene (+Csy4) or the HPTII instead of Csy4 (−Csy4) under the control of the p35S promoter. A picture of the same rice protoplasts under bright field (Bright Field) is used as control to show protoplast integrity. Fluorescence imaging was performed using an epifluorescence microscope with GFP filter cube. Scale bar: 50 μm.

Because of the agronomical and economical importance of grasses, we used the same gene cassettes (p35S::Csy4+ pC4H::cogGFP and p35S::HPTII+pC4H::cogGFP) that were used for the tobacco leaf transient expression system and tested Csy4 activity in a rice protoplast expression system. Fluorescence analysis of transformed protoplasts showed that GFP fluorescence was significantly reduced in cells transformed with the gene cassette containing the Csy4 gene, demonstrating that Csy4 was expressed and active to cleave cogGFP mRNA (FIG. 7). As a second verification, we constructed multi-gene cassettes (p35S::Csy4+pZmUbi:: cogGFP and p35S::HPTII+pZmUbi::cogGFP) in which the ubiquitin promoter from *Zea* maize was used to drive cogGFP expression and p35S promoter for that of Csy4 or HPTII in the control cassette. Similar to the results observed with the pC4H promoter driving the expression of cogGFP, no fluorescence, or only a residual fluorescence, was observed in protoplast transformed with the gene cassette containing the Csy4 coding sequence (data not shown).

Csy4 Orthologs Showed Transgene Repression Activity in Tobacco Leaves

Figure 8A:
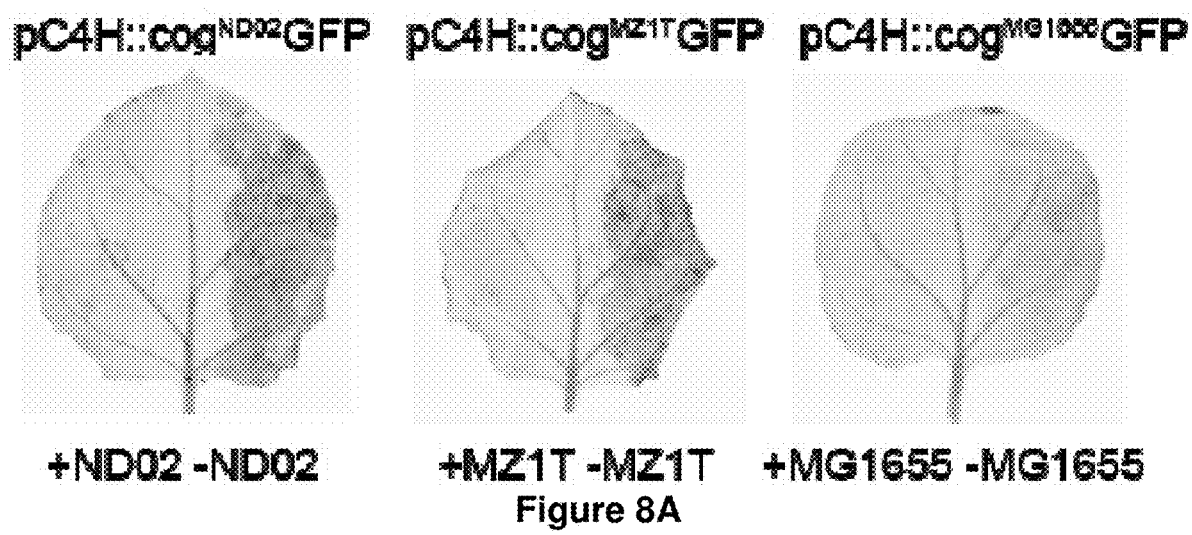
FIG. 8A. Repression activity of Csy4 orthologs. Representative GFP fluorescence images of tobacco leaves infiltrated with Agrobacterium harboring a T-DNA containing a cogGFP (cog$^{ND02}$GFP, cog$^{MZIT}$GFP or cog$^{MG1655}$GFP) and corresponding Csy4 ortholog (+ND02, +MZIT, +MG1655; left side of the leaves), or HPTII (−ND02, −MZIT, −MG1655; right side of the leaves) genes. The cogGFP and Csy4 orthologous genes were under the control of the Arabidopsis C4H promoter (pC4H) and the p35S promoter respectively. Fluorescence imaging of whole leaves was performed as described in FIGS. 2A and 2B.
Figure 8B:
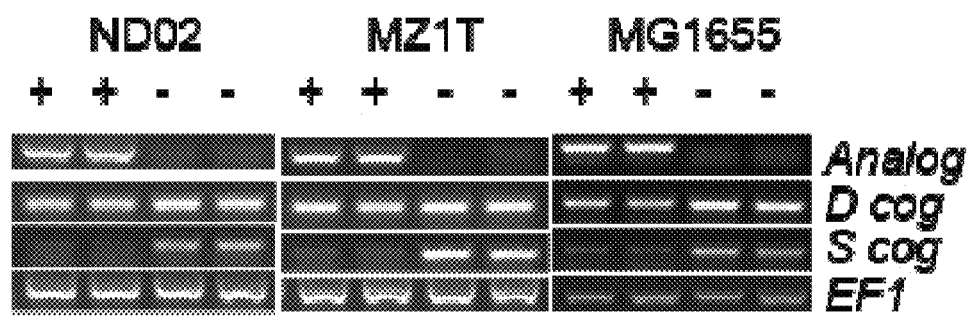
FIG. 8B. Repression activity of Csy4 orthologs. Expression analysis of tobacco leaves infiltrated with Agrobacterium harboring a T-DNA containing a cogGFP (cog$^{ND02}$GFP, cog$^{MZIT}$GFP or cog$^{MG1655}$GFP) and corresponding Csy4 ortholog (+ND02, +MZIT, +MG1655; left side of the leaves), or HPTII (−ND02, −MZIT, −MG1655; right side of the leaves) genes. The cogGFP and Csy4 orthologous genes were under the control of the Arabidopsis C4H promoter (pC4H) and the p35S promoter respectively. Semi-quantitative RT-PCR analysis of cogGFP transcript cleavage in the presence or absence of Csy4 ortholog was performed as described in FIG. 3B.
Figure 11:
FIG. 11. Csy4 orthologous candidates. Fifty-four potential endoribonucleases were aligned by putative CRISPR recognition sequence. The tree was rooted at the midpoint and the branches are transformed for scale. Pseudomonas aeruginosa and the six orthologs chosen for testing in tobacco are highlighted.
Figure 12A:
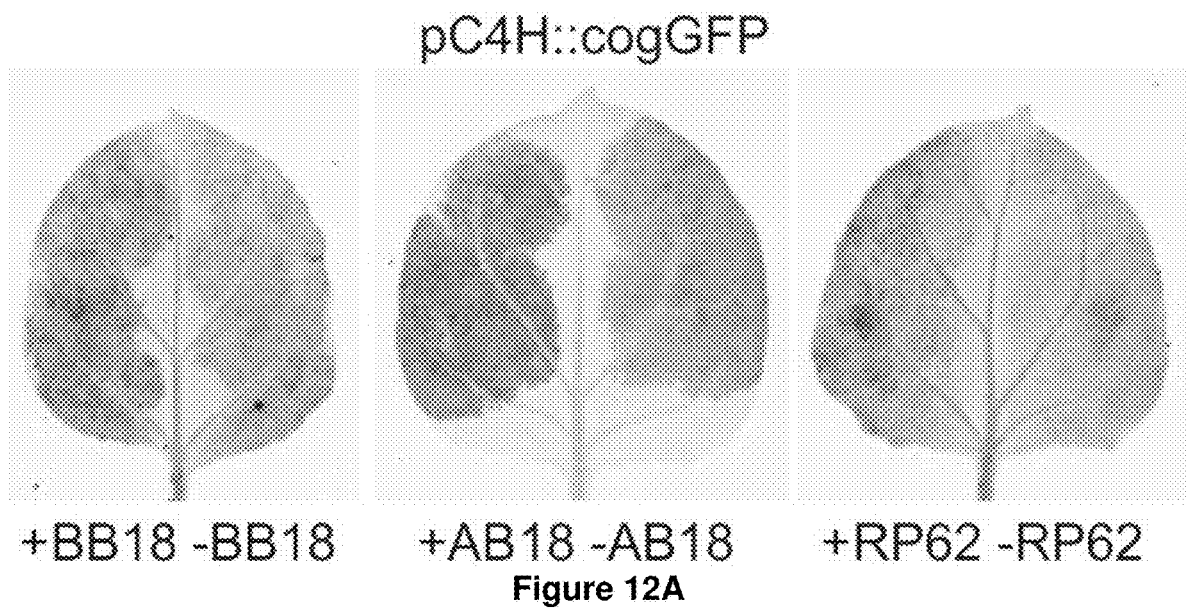
FIG. 12A. Repression activity of Csy4 orthologs BBH18, AB18 and RP62. Representative GFP fluorescence images of tobacco leaves infiltrated with Agrobacterium harboring a T-DNA containing a cogGFP (cog$^{BBH18}$GFP, cog$^{AB18}$GFP or cog$^{RP62}$GFP) and corresponding Csy4 ortholog (+BB18, +AB18, +RP62; left side of the leaves), or HPTII (−BB18, −AB18, −RP62; right side of the leaves) genes. The cogGFP and Csy4 orthologs were under the control of the Arabidopsis C4H promoter (pC4H) and the p35S promoter respectively. Fluorescence imaging was performed as described in FIGS. 2A and 2B.
Figure 12B:
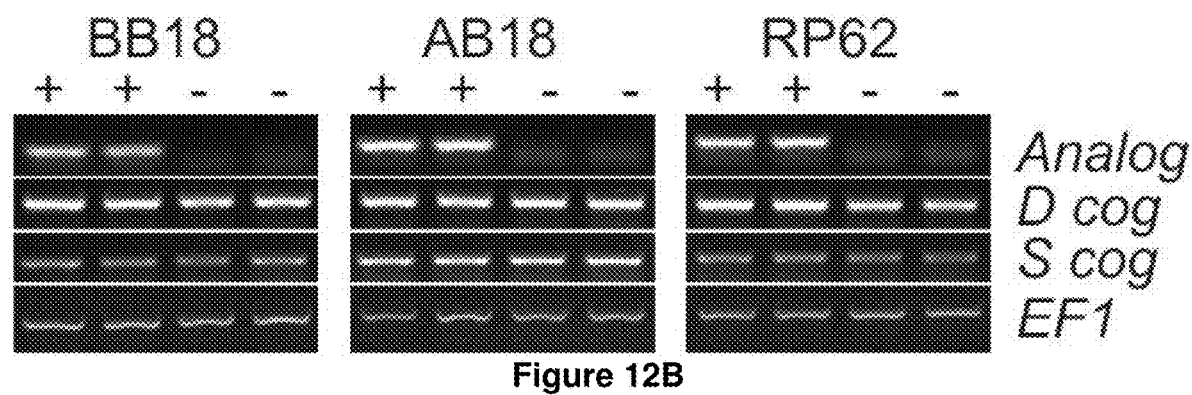
FIG. 12B. Repression activity of Csy4 orthologs BBH18, AB18 and RP62. Expression analysis of tobacco leaves infiltrated with Agrobacterium harboring a T-DNA containing a cogGFP (cog$^{BBH18}$GFP, cog$^{AB18}$GFP or cog$^{RP62}$GFP) and corresponding Csy4 ortholog (+BB18, +AB18, +RP62; left side of the leaves), or HPTII (−BB18, −AB18, −RP62; right side of the leaves) genes. The cogGFP and Csy4 orthologs were under the control of the Arabidopsis C4H promoter (pC4H) and the p35S promoter respectively. Semi-quantitative RT-PCR analysis of cogGFP transcript cleavage in the presence or absence of Csy4 ortholog was performed as described in FIG. 3B.

To find other candidate endoRNase enzymes to build additional and independent two-component repressor systems for plants, we performed a bioinformatics analysis of sequenced CRISPR/Cas systems known to use endoRNases to process CRISPR transcripts. The enzymes themselves are annotated by different names and may or may not align well to each other; orthologs have historically been identified more by position in the Cas cassette than by amino acid sequence and are thus called Csy4, Cas6f, CasE, or Cse3, even when they have identical protein sequences (27, 43). We cross-referenced unique protein sequences from relevant KEGG orthology groups (38) with unique CRISPR repeats from CRISPRdb (39) and kept only those that came from mesophilic hosts. We identified and clustered the 54 enzymes that survived screening by recognition sequence alignment (FIG. 11). Candidate recognition sequences from each branch of the resulting tree were found in plant genomes by BLAST against PlantGDB. Six Csy4 orthologs were selected and codon optimized during synthesis for expression in our plant model system (FIGS. 8A and 8B). Two orthologous two-component repressor systems showed repression of transgenes containing their respective recognition sequence in the 5' UTR of the reporter gene GFP: a CasE from *Lactobacillus delbrueckii* ND02 (GenBank accession number WP_013439422.1) and a CasE from *Thauera aminoaromatica* MZIT (GenBank accession number WP_012585437.1). A third was identified as a CasE from *Escherichia coli* MG1655 (GenBank accession number NP_417236.1) but the presence of the recognition sequence in the 5' UTR of the reporter gene GFP was negatively impacting the expression level of the GFP protein. GFP fluorescence was further reduced when the endoRNase MG1655 was co-expressed (FIG. 8A and FIG. 8B). RT-PCR analysis confirmed that the orthologous two-component repressor systems derived from *L. delbrueckii* ND02, *T. aminoaromatica* MZIT, and *E. coli* MG1655 were able to cleave the 5'UTR of the reporter gene GFP. In contrast, the other three orthologous systems did not show cleavage activity of their predicted recognition sites, which is in agreement with the poor or lack of any reduction in GFP fluorescence reduction (FIG. 12A-B).

DISCUSSION

One of the aims of plant synthetic biology is to provide genetic devices that allow precise gene expression regulation to support plant metabolic engineering, agronomical trait improvement, and development of novel traits in crops (51). In contrast to the microbial field, the application of synthetic biology on plants is rather limited, mainly due to the poor availability of tools (52). Here we present new genetic devices based on a two-component system that uses an endoRNase and its specific recognition site. We built one of these devices using Csy4, the Cas6 endoribonuclease from *P. aeruginosa*, which has an ability to recognize and cleave with precision a 28-nucleotide RNA sequence, and we showed that it could be used to repress expression of transgenes with high efficiency in plants. Very high performance of transcript cleavage by Csy4 was confirmed by RT-PCR, since either no amplification or negligible amplification at the recognition site was observed when Csy4 is expressed. The insertion of endoRNase recognition site at the end of the 5'UTR of the mRNA allows not only the deletion of the 5' UTR but also the de-capping of the transgene transcript. Consequently, the design limits nucleus-cytosol translocation (53), reduces transcript stability (54), and prevents the formation of both the cap-binding complex (55,56) and the translation initiation complex (57, 58), thereby eliminating the transgene product. Moreover, the insertion of the recognition sequence in the 5'UTR also avoids the modification of the protein sequence of the target gene, thus preventing protein inactivation, mistargeting and/ or destabilization. For all three reporter-genes tested (cogGFP, cogRFP, and cogFLUC), we consistently observed the nearly complete if not total elimination of transgene products when Csy4 was co-expressed in the same cells. Meanwhile, the accumulation of transgene products, as measured by fluorescence or luminescence, was not affected by the insertion of the recognition sequence in the 5'UTR in the absence of the specific endoRNase.

Csy4 represses transgene expression by specific 5'UTR removal, thus the repression efficiency was analyzed by quantification of transgene products (fluorescence and luminescence) and 5'UTR integrity of transgene mRNAs with or without Csy4 co-expression. Real-time qPCR analysis showed that for cogGFP and cogRFP genes, each individually expressed under the control of the strong pNOS promoter, constitutive expression of Csy4 leads up to 400-fold reductions of full-length transcript accumulations. Quantification of transgene products measured by fluorescence shows a deep reduction, if not complete elimination, of reporter proteins when Csy4 is co-expressed, which is consistent with the qPCR analysis. The co-expression of Csy4 led to a greater full-length transcript reduction of transgenes when the transgenes were driven by a very strong promoter, pNOS, in comparison to when the same transgene was driven by a weaker promoter, pC4H. This suggests that the amount of Csy4 protein was not limiting, and that the repression magnitude will be determined by the amount of mRNA and saturation of Csy4 catalytic activity.

Similar to LacI and TetR repressor systems (12,13), Csy4-dependent repression is designed as a two-component system, composed of a regulatory sequence and an effector protein. We have shown that the Csy4 recognition sequence can be conveniently inserted upstream of the start codon in the 5'UTR without affecting the expression of the target gene, while exerting efficient repression in the presence of the Csy4 protein. Moreover, we demonstrated the universality of our two-component repression system based on Csy4, as we showed that it could be used to control multiple transgenes simultaneously that were under the control of different promoters. In contrast, LacO and TetO sequences—the DNA motifs recognized by LacI and TetR, respectively—need to be inserted into regulatory regions of the promoters driving the transgene to be regulated by those LacI and TetR repressors. Incorporation of LacO and TetO DNA domains into promoters is context-dependent and requires optimization for each synthetic promoter to be efficiently repressed by the LacI and TetR repressor proteins (12,59). To date, the use of LacO/LacI and TetO/TetR two-component systems is typically coupled with a small number of well-characterized minimal-promoters (12,13,60-62), but their application for other promoters is rather limited. In addition, unlike promoter-based repression systems such as the LacO/LacI and TetO/TetR systems, Csy4 repression works at a post-transcriptional level, offering additional regulatory options. Layered regulation enhances precise expression of transgenes and metabolic pathways by facilitating accurate spatial, temporal, or conditional control of transgene expression. Recently, a non-leaky, inducible transgene expression system was developed based on the combination of chemical induction and alternative splicing machinery (1,63). Layered expression regulation also increases engineering flexibility. For example, if multiple transgenes in a synthetic circuit are co-regulated at the transcriptional level, one or more of these transgenes can be independently repressed by the insertion of the Csy4 recognition sequence and a conditionally expressed Csy4 protein, or by the use of other Csy4 orthologous two-component repressor systems.

The successful application in transiently and stably transformed plant-cell hosts composed of monocot and dicot plant species further support the robustness and efficiency of this two-component repressor device. We have shown that very strong and specific repression can be achieved when two transgenes of interest and Csy4 were driven by constitutive promoters as well as when Csy4 was under the control of a cell-specific promoter. It has not been tested and it is unknown how many mRNAs a single Csy4 protein can cleave. Thus it is plausible that, under specific conditions, transgene repression would not be complete if the Csy4 were poorly expressed, and the amount of Csy4 protein was limited relative to the abundance transgene transcript containing the recognition site. In the case of limiting Csy4 protein amount and a full repression need, the Csy4 protein level could be enhanced without the need for the identification of a new promoter. Increased Csy4 expression could be achieved by the insertion of an exon in the encoding sequence (64) or the use of viral 5'UTR and 3'UTR that would boost mRNA stability and translation efficiency (65, 66). Alternatively, for an extremely weak promoter driving the expression of Csy4, a virus-vector assisted activation technology (67) could be applied to boost the accumulation of Csy4 protein and reach the required protein amount for complete transgene transcript elimination. It should be noted that even partial repression could be beneficial for situations when the product of the transgene regulated by Csy4 activity is essential.

The identification of 54 independent two-component expression-repressor systems, and the validation of three of them (out of six tested), exhibit the great potential for plant metabolic engineering and the development of layer expression regulation. It will allow the construction of several independent two-component expression-repressor systems for independent regulation of various transgenes, but also the design of single or multiple transgenes that can be regulated by multiple factors. For example, different recognition sequences could be inserted in the 5'UTR and 3'UTR of the transgene, and each recognition sequence would be cleaved by its specific endoRNase, under the control of specific promoters. In addition, they could be used to create degrees of conditional repression of transgenes to fine-tune engineered metabolic pathways. This would be achieved with the use of different promoters to control the expression of endoRNases, each exhibiting the different cleavage efficiency of their respective recognition sequences; or by a strategy of independent repression (e.g., the use of two endoRNases, each controlling the deletion of 5'UTR or 3'UTR).

The use of such two-component expression-repressor systems is not limited to the regulation of metabolic pathways. It could be deployed to control the expression of toxic proteins. For example, it could be used to control the expression of a toxic protein used to generate male sterility in crops, such as the bacterial cytotoxic ribonuclease (Barnase) or the *Arabidopsis* autophagy-related gene BECLIN1 (68, 69). This could be achieved by the insertion of the endoRNase recognition sequences in the 5'UTR of the mRNA encoding the toxic protein, and the generation of two independent crop lines. One (female line) would harbor the toxin gene expressed in the anther tapetum tissue, causing male sterility due to tapetum degeneration. The second line (male line) would express the specific endoRNase in the same tissue. The F1 population resulting from the crossing of both engineered parents would be fertile, because the endoRNase would block the production of the toxic protein and allow normal tapetal development. Such a system would support general breeding programs and the development of hybrid crops exhibiting so-called "hybrid vigor." While keeping the breeding option, this controlled fertility presents an opportunity to develop sterile energy crops used for cellulosic biofuels and avoid gene flow from crops to wild relatives, which is a major limitation in the attempts to engineer energy crops such as sorghum.

Besides regulating protein-encoding RNAs, Csy4-mediated transcript cleavage may be applied for the regulation of other functional RNAs. For instance, the precursor of microRNAs, pre-miRNAs, share the common 5'-capping feature as pre-mRNAs (70) and are likely to be subjected to Csy4 repression with the recognition sequence inserted in the 5' UTR. Cleavage activity of Csy4 has been deployed in human cells for the production of multiple guide RNAs from a single transcript in CRISPR/CAS targeting (71), and it may function as well in plants.

The rational design and engineering of biological devices requires well-characterized and robust regulatory parts (72). Our study in plants, when coupled with previous work in bacteria (30,31), yeast (30), and mammalian cells (32, 71), suggests that the Csy4 protein and its recognition sequence are a universal two-component repressor device for the efficient genetic engineering of diverse organisms. We also identified several new two-component repressor systems, orthologous to Csy4, and already validated the functionality of some them in planta. We believe that several of them will be as universal as the Csy4 system. The availability of multiple two-component repressor systems could be used in a single organism to create complex and universal regulatory circuits to control diverse metabolic pathways.

TABLE 1

Expression clones and the construction clones. For simplicity, terminators are not indicated.

(i) Expression clones by regular Gateway recombination reaction.

| # | Expression Clone | Expression Vector | Entry Clone |
|---|---|---|---|
| C68 | pTKan-p355::Csy4 | pTKan-p355::attR1-GW-attR2 | pDONR221-att1-Csy4-att2 |
| C97 | pTKan-p355::Csy4::YFP | pTKan-p355::attR1-GW-attR2::YFP | pDONR221-att1-Csy4-att2 |

(ii) Expression clones by multi-site Gateway recombination reaction.

| # | Expression Clone | Expression Vector | Entry Clone 1 | Entry Clone 2 | Entry Clone 3 |
|---|---|---|---|---|---|
| C44 | pTKan-p35S::Csy4-pC4H::cogGFP | pTKan-p35S::attR1-GW-attR2 | pDONR221-attL1-Csy4-attL4 | pDONR221-attR4-pC4H-attR3 | pDONR221-attL3-cogGFP-attL2 |
| C45 | pTKan-p35S::HPTII-pC4H::cogGFP | pTKan-p35S::attR1-GW-attR2 | pDONR221-attL1-HPTII-attL4 | pDONR221-attR4-pC4H-attR3 | pDONR221-attL3-cogGFP-attL2 |
| C90 | pTKan-p35S::Csy4-pC4H::cogRFP | pTKan-p35S::attR1-GW-attR2 | pDONR221-attL1-Csy4-attL4 | pDONR221-attR4-pC4H-attR3 | pDONR221-attL3-cogRFP-attL2 |
| C91 | pTKan-p35S::HPTII-pC4H::cogRFP | pTKan-p35S::attR1-GW-attR2 | pDONR221-attL1-HPTII-attL4 | pDONR221-attR4-pC4H-attR3 | pDONR221-attL3-cogRFP-attL2 |
| C132 | pTKan-p35S::Csy4-pNOS::cogGFP | pTKan-p35S::attR1-GW-attR2 | pDONR221-attL1-Csy4-attL4 | pDONR221-attR4-pNOS-attR3 | pDONR221-attL3-cogGFP-attL2 |
| C134 | pTKan-p35S::Csy4-pNOS::cogRFP | pTKan-p35S::attR1-GW-attR2 | pDONR221-attL1-Csy4-attL4 | pDONR221-attR4-pNOS-attR3 | pDONR221-attL3-cogRFP-attL2 |
| C135 | pTKan-p35S::HPTII-pNOS::cogGFP | pTKan-p35S::attR1-GW-attR2 | pDONR221-attL1-HPTII-attL4 | pDONR221-attR4-pNOS-attR3 | pDONR221-attL3-cogGFP-attL2 |
| C137 | pTKan-p35S::HPTII-pNOS::cogRFP | pTKan-p35S::attR1-GW-attR2 | pDONR221-attL1-HPTII-attL4 | pDONR221-attR4-pNOS-attR3 | pDONR221-attL3-cogRFP-attL2 |
| C285 | pTKan-p35S::RFP-p35S::Csy4-pZmUbi::cogGFP | pTKan-p35S::RFP-p35S::attR1-GW-attR2 | pDONR221-attL1-Csy4-attL4 | pDONR221-attR4-pZmUbi-attR3 | pDONR221-attL3-cogGFP-attL2 |
| C286 | pTKan-p35S::RFP-p35S::HPTII-pZmUbi::cogGFP | pTKan-p35S::RFP-p35S::attR1-GW-attR2 | pDONR221-attL1-HPTII-attL4 | pDONR221-attR4-pZmUbi-attR3 | pDONR221-attL3-cogGFP-attL2 |
| C310 | pTKan-pNOS::RFP-p35S::cogGFP2AGUS-pGCI::Csy4 | pTKan-pNOS::RFP-p35S::attR1-GW-attR2 | pDONR221-attL1-cogGFP2AGUS-attL4 | pDONR221-attR4-pGC1-attR3 | pDONR221-attL3-Csy4-attL2 |
| C311 | pTKan-pNOS::RFP-p35S::cogGFP2AGUS-pGCI::HPTII | pTKan-pNOS::RFP-p35S::attR1-GW-attR2 | pDONR221-attL1-cogGFP2AGUS-attL4 | pDONR221-attR4-pGC1-attR3 | pDONR221-attL3-HPTII-attL2 |
| C323 | pTKan-p35S::BBH18-pC4H::cogBBH18GFP | pTKan-p35S::attR1-GW-attR2 | pDONR221-attL1-BBH18-attL4 | pDONR221-attR4-pC4H-attR3 | pDONR221-attL3-cogBBH18GFP-attL2 |

TABLE 1-continued

Expression clones and the construction clones. For simplicity, terminators are not indicated.

| | | | | | |
|---|---|---|---|---|---|
| C324 | pTKan-p35S::ND02-pC4H::cogND02GFP | pTKan-p35S::attR1-GW-attR2 | pDONR221-attL1-ND02-attL4 | pDONR221-attR4-pC4H-attR3 | pDONR221-attL3-cogND02GFP-attL2 |
| C325 | pTKan-p35S::AB18-pC4H::cogAB18GFP | pTKan-p35S::attR1-GW-attR2 | pDONR221-attL1-AB18-attL4 | pDONR221-attR4-pC4H-attR3 | pDONR221-attL3-cogAB18GFP-attL2 |
| C326 | pTKan-p35S::RP62-pC4H::cogRP62GFP | pTKan-p35S::attR1-GW-attR2 | pDONR221-attL1-RP62-attL4 | pDONR221-attR4-pC4H-attR3 | pDONR221-attL3-cogRP62GFP-attL2 |
| C328 | pTKan-p35S::MZ1T-pC4H::cogMZ1TGFP | pTKan-p35S::attR1-GW-attR2 | pDONR221-attL1-MZ1T-attL4 | pDONR221-attR4-pC4H-attR3 | pDONR221-attL3-cogMZ1TGFP-attL2 |
| C329 | pTKan-p35S::MG1655-pC4H::cogMG1655GFP | pTKan-p35S::attR1-GW-attR2 | pDONR221-attL1-MG1655-attL4 | pDONR221-attR4-pC4H-attR3 | pDONR221-attL3-cogMG1655GFP-attL2 |
| C330 | pTKan-p35S::HPTII-pC4H::cogBBH18GFP | pTKan-p35S::attR1-GW-attR2 | pDONR221-attL1-HPTII-attL4 | pDONR221-attR4-pC4H-attR3 | pDONR221-attL3-cogBBH18GFP-attL2 |
| C331 | pTKan-p35S::HPTII-pC4H::cogND02GFP | pTKan-p35S::attR1-GW-attR2 | pDONR221-attL1-HPTII-attL4 | pDONR221-attR4-pC4H-attR3 | pDONR221-attL3-cogND02GFP-attL2 |
| C332 | pTKan-p35S::HPTII-pC4H::cogAB18GFP | pTKan-p35S::attR1-GW-attR2 | pDONR221-attL1-HPTII-attL4 | pDONR221-attR4-pC4H-attR3 | pDONR221-attL3-cogAB18GFP-attL2 |
| C333 | pTKan-p35S::HPTII-pC4H::cogRP62GFP | pTKan-p35S::attR1-GW-attR2 | pDONR221-attL1-HPTII-attL4 | pDONR221-attR4-pC4H-attR3 | pDONR221-attL3-cogRP62GFP-attL2 |
| C335 | pTKan-p35S::HPTII-pC4H::cogMZ1TGFP | pTKan-p35S::attR1-GW-attR2 | pDONR221-attL1-HPTII-attL4 | pDONR221-attR4-pC4H-attR3 | pDONR221-attL3-cogMZ1TGFP-attL2 |
| C336 | pTKan-p35S::HPTII-pC4H::cogMG1655GFP | pTKan-p35S::attR1-GW-attR2 | pDONR221-attL1-HPTII-attL4 | pDONR221-attR4-pC4H-attR3 | pDONR221-attL3-cogMG1655GFP-attL2 |
| C352 | pTKan-pNOS::RFP-p35S::GVG-pUAS::Csy4-pC4H::cogFLUC | pTKan-pNOS::RFP-p35S::GVG-pUAS::attR1-GW-attR2 | pDONR221-attL1-Csy4-attL4 | pDONR221-attR4-pC4H-attR3 | pDONR221-attL3-cogFLUC-attL2 |
| C354 | pTKan-pNOS::RFP-p35S::GVG-pUAS::HPTII-pC4H::cogFLUC | pTKan-pNOS::RFP-p35S::GVG-pUAS::attR1-GW-attR2 | pDONR221-attL1-HPTII-attL4 | pDONR221-attR4-pC4H-attR3 | pDONR221-attL3-cogFLUC-attL2 |
| C358 | pTKan-pAct2::cogRFP-p35S::cogGFP-pNOS::Csy4 | pTKan-pAct2::cogRFP-p35S::attR1-GW-attR2 | pDONR221-attL1-cogGFP-attL4 | pDONR221-attR4-pNOS-attR3 | pDONR221-attL3-Csy4-attL2 |
| C359 | pTKan-pAct2::cogRFP-p35S::cogGFP-pNOS::HPTII | pTKan-pAct2::cogRFP-p35S::attR1-GW-attR2 | pDONR221-attL1-cogGFP-attL4 | pDONR221-attR4-pNOS-attR3 | pDONR221-attL3-HPTII-attL2 |
| C360 | pTKan-p35S::HPTII-pC4H::GFP | pTKan-p35S::attR1-GW-attR2 pDONR221-attL1-HPTII-attL4 | pDONR221-attL1-HPTII-attL | pDONR221-attR4-pC4H-attR3 | pDONR221-attL3-GFP-attL2 |
| C361 | pTKan-p35S::HPTII-pC4H::RFP | pTKan-p35S::attR1-GW-attR2 pDONR221-attL1-HPTII-attL4 | pDONR221-attL1-HPTII-attL4 | pDONR221-attR4-pC4H-attR3 | pDONR221-attL3-RFP-attL2 |
| C362 | pTKan-p35S::HPTII-pC4H::FLUC | pTKan-p35S::attR1-GW-attR2 pDONR221-attL1-HPTII-attL4 | pDONR221-attL1-HPTII-attL4 | pDONR221-attR4-pC4H-attR3 | pDONR221-attL3-FLUC-attL2 |
| C363 | pTKan-p35S::HPTII-pC4H::cogFLUC | pTKan-p35S::attR1-GW-attR2 | pDONR221-at | pDONR221-attR4-pC4H-attR3 | pDONR221-attL3-cogFLUC-attL2 |

TABLE 1-continued

Expression clones and the construction clones. For simplicity, terminators are not indicated.

| C365 | pTKan-p35S::Csy4-pC4H::cogFLUC | pTKan-p35S::attR1-GW-attR2 | pDONR221-attL1 | pDONR221-attR4-pC4H-attR3 | pDONR221-attL3-cogFLUC-attL2 |
|---|---|---|---|---|---|

TABLE 2

Primer list.

| Name | Experiment, 5'->3' sequence | Tm | Site |
|---|---|---|---|
| BP cloning of pDONR221-attB3-NLSCSY4-attB2 | | 65 | |
| attb3-CSY4Nuc-F | gacaactttgtataataaagttggcatggctccaaaaaagaaaagaaagg (SEQ ID NO: 2) | | AttB3 |
| attb2-CSY4Nuc-R | gaccactttgtacaagaaagctgggtctcagaaccaaggcacgaatc (SEQ ID NO: 3) | | AttB2 |
| BP cloning of pDONR221-attB3-HPTII-attB2 | | 62 | |
| attb3-Hygr-F | gacaactttgtataataaagttggcatgaaaaagcctgaactcacc (SEQ ID NO: 4) | | AttB3 |
| attb2-Hygr-R | gaccactttgtacaagaaagctgggtcttttctttgccctcggacg (SEQ ID NO: 5) | | AttB2 |
| BP cloning of pDONR221-attB3-RFP-attB2 | | 65 | |
| attB3-RFP-F | gacaactttgtataataaagttggcatggcctcctccgagaac (SEQ ID NO: 6) | | AttB3 |
| R-attB2-RFP | gaccactttgtacaagaaagctgggtccaggaacaggtggtggcg (SEQ ID NO: 7) | | AttB2 |
| Subcloning of cogGFP-attB2 | | 58 | |
| F-cogGFP-F | cgttcactgccgtataggcagctaagaaatatggtgagcaagggcgagg (SEQ ID NO: 8) | | |
| R-attB2-GFP | accactttgtacaagaaagctgggtacttgtacagctcgtccatgcc (SEQ ID NO: 9) | | AttB2 |
| Subcloning of cogRFP-attB2 | | 65 | |
| F-csycog-RFP (in pair with R-attB2-RFP) | cgttcactgccgtataggcagctaagaaatatggcctcctccgagaac (SEQ ID NO: 10) | | |
| Subcloning of cogFLuc-attB2 | | 59 | |
| F-cogFFLuc-F | cgttcactgccgtataggcagctaagaaatatggttactgatgctaaaaatat-taag (SEQ ID NO: 11) | | |
| R-attB2-FFLuc | gaccactttgtacaagaaagctgggtctcacagcgatctttcctc (SEQ ID NO: 12) | | |
| BP cloning of pDONR221-attB3-cogGFP/RFP/FLuc-attB2 | | 64 | |
| F-attB3-csycog (in pair with R-attB2-GFP/RFP/FLuc) | gacaactttgtataataaagttggccgttcactgccgtataggc (SEQ ID NO: 13) | | AttB3 |
| Infusion cloning of pTKan-pAct2-cogRFP-tNOS-p35S-attR1-GW-attR2 Amplification of pAct2 | | 62 | |
| F-pTKan-ApaIe-pAct2 (ApaI eliminated) | ggggatcctctagagggagtcgacaaaatttagaacg (SEQ ID NO: 14) | | |
| R-cog-pAct2 | gcctatacggcagtgaacgttcaaagcggagaggaaaatatatg (SEQ ID NO: 15) | | |
| Amplification of cogRFP | | 65 | |
| R-tNOS-pTKan-ApaI (in pair with F-csycog-RFP) | tccgcggacgtcccgggcccGAGCTTGCATGCCGGTCG (SEQ ID NO: 16) | | ApaI |

TABLE 2 -continued

Primer list.

| Name | Experiment, 5'->3' sequence | Tm | Site |
|---|---|---|---|
| Infusion cloning of pGCI into pDON-tG7-pGCI B4rB3r construct | | 57 | |
| F-tG7-pGCI | tgtaccccgggtaccaagcttgagtaaagattcagtaacccg (SEQ ID NO: 17) | | HindIII |
| R-attR3-pGCI | tattatacaaagttgtcctaggattcttgagtagtgattttgaag (SEQ ID NO: 18) | | AvrII |
| Infusion cloning of pGmUbi into pDON-tG7-pGmUbi B4rB3r construct | | 62 | |
| F-tG7-pGmUbi | tgtaccccgggtaccaagcttcagtgcagcgtgacccg (SEQ ID NO: 19) | | HindIII |
| R-attR3-pGmUbi | tattatacaaagttgtcctaggggatcctctagagtcgacctg (SEQ ID NO: 20) | | AvrII |
| RT-PCR of cogGFP, primers spanning the cleavage site | | 54 | |
| pC4H3UTR-F | ctcagcagcttcttctgc (SEQ ID NO: 21) | | |
| GFP92R | gacacgctgaacttgtgg (SEQ ID NO: 22) | | |
| RT-PCR of cogGFP, primers downstream of the cleavage site | | 55 | |
| GFP455F | atatcatggccgacaagcag (SEQ ID NO: 23) | | |
| GFP643R | tctcgttggggtctttgctc (SEQ ID NO: 24) | | |
| RT-PCR of CSY4 | | 57 | |
| CSY4-62F | agacccagagttccctccag (SEQ ID NO: 25) | | |
| CSY4-237R | agccctaaggtcatctgctg (SEQ ID NO: 26) | | |
| RT-PCR and qPCR of cogRFP, primers spanning the cleavage site | | 54 | |
| RFP89R (in pair with pC4H3UTR-F) | tcgatctcgaactcgtggcc (SEQ ID NO: 27) | | |
| RT-PCR of cogRFP, primers downstream of the cleavage site | | 58 | |
| RFP661F | catcaagttggacatcacctc (SEQ ID NO: 28) | | |
| attB2R | ccactttgtacaagaaagctgg (SEQ ID NO: 29) | | |
| RT-PCR of EF1 | | 63 | |
| EF1New-F | agggtccaaccctccttgaggc (SEQ ID NO: 30) | | |
| EF1New-R | gccccttggctgggtcgtc (SEQ ID NO: 31) | | |
| RT-PCR of ND02 | | 56 | |
| ND02-q1F | caagttgaccgcaaatcctgt (SEQ ID NO: 32) | | |
| ND02-q1R | ctgcttttccctgcaaccac (SEQ ID NO: 33) | | |
| RT-PCR of MZ1T | | 58 | |
| MZ1T-q1F | gcaaggggagatgcagctaa (SEQ ID NO: 34) | | |
| MZ1T-q1R | cactctctgagcaggccttc (SEQ ID NO: 35) | | |

TABLE 2 -continued

Primer list.

| Name | Experiment, 5'->3' sequence | Tm | Site |
|---|---|---|---|
| qPCR of KAN | | 60 | |
| Kan-q1F | atctcctgtcatctcaccttgc (SEQ ID NO: 36) | | |
| Kan-q1R | tttcgcttggtggtcgaatg (SEQ ID NO: 37) | | |
| qPCR of CSY4 | | 60 | |
| CSY4-q1F | agctttggttgcacaaggtg (SEQ ID NO: 38) | | |
| CSY4-q1R | aaagccctaaggtcatctgctg (SEQ ID NO: 39) | | |
| qPCR of cogGFP | | 60 | |
| attB3-cog | taaagttggccgttcactgc (SEQ ID NO: 40) | | |
| pC4H-cogGFP_1R | aacttgtggccgtttacgtc (SEQ ID NO: 41) | | |
| qPCR of cogRFP | | 60 | |
| attB3-cog (in pair with RFP89R) | See the same primers above | | |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A host cell comprising:
(a) first polynucleotide comprising a first promoter operatively linked to an open reading frame (ORF) encoding an endoribonuclease, or an enzymatic active fragment thereof, which cleaves a recognition sequence; and
(b) a second polynucleotide comprising a second promoter operatively linked to a nucleotide sequence comprising, in a 5' to 3' order:
(i) a 5' untranslated region (UTR), the recognition sequence, and a coding sequence of interest,
(ii) a 5' UTR, a first coding sequence of interest, a UTR with the recognition sequence within the UTR, and a second coding sequence of interest, or
(iii) a 5' UTR, a localization sequence (LS) with the recognition sequence within the LS, and a coding sequence of interest; wherein:
(A) the host cell further comprises: (c) a third polynucleotide comprising a third promoter operatively linked to a nucleotide sequence comprising, in a 5' to 3' order: (i) a 5' untranslated region (UTR), the recognition sequence, and a coding sequence of interest, (ii) a 5' UTR, a first coding sequence of interest, a UTR with the recognition sequence within the UTR, and a second coding sequence of interest, or (iii) a 5' UTR, a localization sequence (LS) with the recognition sequence within the LS, and a coding sequence of interest;
(B) the LS is a LS that targets the coding sequence of interest to a plastid;
(C) the second polynucleotide encodes a second promoter operatively linked to a nucleotide sequence comprising, in a 5' to 3' order, a 5' UTR, a first coding sequence of interest, a UTR with the recognition sequence within the UTR, and a second coding sequence of interest; wherein when a transcript is transcribed from the second promoter, and (i) when the endoribonuclease is not expressed from the first polynucleotide, the endoribonuclease cleaves the recognition sequence in the transcript, and the first coding sequence of interest is translated while the second coding sequence of interest is not translated, and (ii) when the endoribonuclease is expressed from the first polynucleotide, and both the first coding sequence of interest and the second coding sequence of interest are translated;
or
(D) the second polynucleotide encodes a second promoter operatively linked to a nucleotide sequence comprising, in a 5' to 3' order, a 5' UTR, a localization sequence (LS) with the recognition sequence within the LS, and a coding sequence of interest; wherein when a transcript is transcribed from the second promoter, and (i) when the endoribonuclease is expressed from the first polynucleotide, the endoribonuclease cleaves the recognition sequence in the transcript, and the coding sequence of interest is translated and is cystolic, and (ii) when the endoribonuclease is not expressed from the first polynucleotide, and the coding sequence of interest is translated and targeted to an organelle by the LS;
wherein the host cell is a plant cell.

2. The host cell of claim 1, wherein the endoribonuclease is an endoribonuclease encoded by *Shewanella* sp. shn csy4, *Citrobacter koseri* cko csy4, *Moraxella catarrhalis* mct csy4, *Acinetobacter baumannii* aby csy4, *Psychrobacter* sp. pso csy4, *Selenomonas ruminantium* sri csy4, *Pseudomonas aeruginosa* pau csy4, *Shewanella piezotolerans* swp csy4, *Streptomyces pratensis* sfa casE, *Streptococcus sanguinis* ssa cas6, *Mycobacterium smegmatis* msa casE, *Streptomyces hygroscopicus* shy casE, *Frankia symbiont* fsy cas6, *Cyanotheca* sp. cyi cas6, *Polymorphum grivum* pgv casE, *Thauera aminoaromatica* tmz casE, *Anaeromyxobacter* sp. ank casE, *Corynebacterium aurimucosum* car casE, *Cellulomonas fimi* cfi casE, *Clostridium* sp. cls casE, *Lactobacillus delbrueckii* ide casE, *Desulfatibacillum alkenivorans* dal casE, *Lactobacillus casei* lca casE, *Arcanobacterium haemolyticum* ahe casE, *Allochromatium vinosum* alv casE, *Verrucosispora maris* vma casE, *Bifidobacterium asteroids* bast casE, *Bifidobacterium animalis* bni casE, *Streptococcus salivarius* ssr casE, *Xenorhabdus bovienii* xbo casE, *Escherichia coli* eco casE, *Salmonella enterica* sega casE, *Cycloclasticus zancles* cza casE, *Dehalococcoides mccarthyi* deh casE, *Lactobacillus fermentum* lff casE, *Arcobacter* sp. arc cas6, *Clostridium novyi* cno cas6, *Clostridium botulinum* cbi cas6, *Campylobacter hominis* cha cas6, *Fusobacterium nucleatum* fnu cas6, *Acetobacterium woodii* awo cas6, *Methanobrevibacter* sp. meb cas6, *Methanobrevibacter smithii* msi cas6, *Methanobacterium* sp. mew cas6, *Brachyspira murdochii* brm cas6, *Geobacillus* sp. get cas6, *Spirosoma linguale* sli cas6, *Finegoldia magna* fma casE, *Fusobacterium nucleatum* fus cas6, *Trichormus azollae* naz cas6, *Campylobacter fetus* camp cas6, *Sulfurospirillum deleyianum* sdl cas6, or *Arcobacter nitrofigitis* ant cas6.

3. The host cell of claim 2, wherein the endoribonuclease is an endoribonuclease encoded by *Shewanella* sp. shn csy4, *Citrobacter koseri* cko csy4, *Moraxella catarrhalis* mct csy4, *Acinetobacter baumannii* aby csy4, *Psychrobacter* sp. pso csy4, *Selenomonas ruminantium* sri csy4, *Pseudomonas aeruginosa* pau csy4, *Shewanella piezotolerans* swp csy4, *Streptomyces pratensis* sfa casE, *Streptococcus sanguinis* ssa cas6, *Mycobacterium smegmatis* msa casE, *Streptomyces hygroscopicus* shy casE, *Frankia symbiont* fsy cas6, *Cyanotheca* sp. cyi cas6, *Polymorphum grivum* pgv casE, *Thauera aminoaromatica* tmz casE, *Anaeromyxobacter* sp. ank casE, *Corynebacterium aurimucosum* car casE, *Cellulomonas fimi* cfi casE, *Clostridium* sp. cls casE, *Lactobacillus delbrueckii* lde casE, *Desulfatibacillum alkenivorans* dal casE, *Lactobacillus casei* lca casE, *Arcanobacterium haemolyticum* ahe casE, *Allochromatium vinosum* alv casE, *Verrucosispora marls* vma casE, *Bifidobacterium asteroids* bast casE, *Bifidobacterium animalis* bni casE, *Streptococcus salivarius* ssr casE, *Xenorhabdus bovienii* xbo casE, *Escherichia coli* eco casE, *Salmonella enterica* sega casE, *Cycloclasticus zancles* cza casE, *Dehalococcoides mccarthyi* deh casE, or *Lactobacillus fermentum* lff casE.

4. The host cell of claim 3, wherein the endoribonuclease is one selected from the group consisting of *Pseudomonas aeruginosa* Csy4, *Moraxella catarrhalis* Csy4, *Escherichia coli* CasE, *Verrucosispora maris* CasE, *Lactobacillus delbrueckii* CasE, and *Thauera aminoaromatica* CasE.

5. The host cell of claim 3, wherein the endoribonuclease is one selected from the group consisting of *Shewanella piezotolerans* Csy4, *Pseudomonas aeruginosa* Csy4, *Selenomonas ruminantium* Csy4, *Psychrobacter* sp. Csy4, and *Acinetobacter baumannii* Csy4.

6. The host cell of claim 1, wherein the second polynucleotide encodes a second promoter operatively linked to a nucleotide sequence comprising, in a 5' to 3' order, a 5' UTR, the recognition sequence, and a coding sequence of interest.

7. The host cell of claim 1, wherein the second polynucleotide encodes a second promoter operatively linked to a nucleotide sequence comprising, in a 5' to 3' order, a 5' UTR, a first coding sequence of interest, a UTR with the recognition sequence within the UTR, and a second coding sequence of interest.

8. The host cell of claim 1, wherein the second polynucleotide encodes a second promoter operatively linked to a nucleotide sequence comprising, in a 5' to 3' order, a 5' UTR, a localization sequence (LS) with the recognition sequence within the LS, and a coding sequence of interest.

9. The host cell of claim 1, wherein the first polynucleotide comprises a LS linked to the 5' end of the endoribonuclease, or the enzymatic active fragment thereof.

10. The host cell of claim 1 further comprising: (c) a third polynucleotide comprising a third promoter operatively linked to a nucleotide sequence comprising, in a 5' to 3' order:

(i) a 5' untranslated region (UTR), the recognition sequence, and a coding sequence of interest, (ii) a 5' UTR, a first coding sequence of interest, a UTR with the recognition sequence within the UTR, and a second coding sequence of interest, or (iii) a 5' UTR, a localization sequence (LS) with the recognition sequence within the LS, and a coding sequence of interest.

11. The host cell of claim 1, wherein the LS is a LS that targets the coding sequence of interest to a plastid.

12. The host cell of claim 1, wherein the second polynucleotide encodes a second promoter operatively linked to a nucleotide sequence comprising, in a 5' to 3' order, a 5' UTR, a first coding sequence of interest, a UTR with the recognition sequence within the UTR, and a second coding sequence of interest; wherein when a transcript is transcribed from the second promoter, and (i) when the endoribonuclease is not expressed from the first polynucleotide, the endoribonuclease cleaves the recognition sequence in the transcript, and the first coding sequence of interest is translated while the second coding sequence of interest is not translated, and (ii) when the endoribonuclease is expressed from the first polynucleotide, and both the first coding sequence of interest and the second coding sequence of interest are translated.

13. The host cell of claim 1, wherein the second polynucleotide encodes a second promoter operatively linked to a nucleotide sequence comprising, in a 5' to 3' order, a 5' UTR, a localization sequence (LS) with the recognition sequence within the LS, and a coding sequence of interest; wherein when a transcript is transcribed from the second promoter, and (i) when the endoribonuclease is expressed from the first polynucleotide, the endoribonuclease cleaves the recognition sequence in the transcript, and the coding sequence of interest is translated and is cystolic, and (ii) when the endoribonuclease is not expressed from the first polynucleotide, and the coding sequence of interest is translated and targeted to an organelle by the LS.

* * * * *

SEQUENCE LISTING

<160> NUMBER OF SEQ ID NOS: 47

<210> SEQ ID NO 1
<211> LENGTH: 187
<212> TYPE: PRT
<213> ORGANISM: Pseudomonas aeruginosa

<400> SEQUENCE: 1

```
Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
```

```
            145                 150                 155                 160
His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185
```

<210> SEQ ID NO 2
<211> LENGTH: 50
<212> TYPE: DNA
<213> ORGANISM: Artificial Sequence
<220> FEATURE:
<223> OTHER INFORMATION: BP cloning of pDONR221-attB3-NLSCSY4-attB2
      forward primer

<400> SEQUENCE: 2
gacaactttg tataataaag ttggcatggc tccaaaaaag aaaagaaagg            50

<210> SEQ ID NO 3
<211> LENGTH: 47
<212> TYPE: DNA
<213> ORGANISM: Artificial Sequence
<220> FEATURE:
<223> OTHER INFORMATION: BP cloning of pDONR221-attB3-NLSCSY4-attB2
      reverse primer

<400> SEQUENCE: 3
gaccactttg tacaagaaag ctgggtctca gaaccaaggc acgaatc               47

<210> SEQ ID NO 4
<211> LENGTH: 46
<212> TYPE: DNA
<213> ORGANISM: Artificial Sequence
<220> FEATURE:
<223> OTHER INFORMATION: BP cloning of pDONR221-attB3-HPTII-attB2
      forward primer

<400> SEQUENCE: 4
gacaactttg tataataaag ttggcatgaa aaagcctgaa ctcacc                46

<210> SEQ ID NO 5
<211> LENGTH: 45
<212> TYPE: DNA
<213> ORGANISM: Artificial Sequence
<220> FEATURE:
<223> OTHER INFORMATION: BP cloning of pDONR221-attB3-HPTII-attB2
      reverse primer

<400> SEQUENCE: 5
gaccactttg tacaagaaag ctgggtcttt ctttgccctc ggacg                 45

<210> SEQ ID NO 6
<211> LENGTH: 43
<212> TYPE: DNA
<213> ORGANISM: Artificial Sequence
<220> FEATURE:
<223> OTHER INFORMATION: BP cloning of pDONR221-attB3-RFP-attB2 forward
      primer

<400> SEQUENCE: 6
gacaactttg tataataaag ttggcatggc ctcctccgag aac                   43

<210> SEQ ID NO 7
<211> LENGTH: 45
<212> TYPE: DNA
<213> ORGANISM: Artificial Sequence
<220> FEATURE:

```
<223> OTHER INFORMATION: BP cloning of pDONR221-attB3-RFP-attB2 reverse
      primer

<400> SEQUENCE: 7
gaccactttg tacaagaaag ctgggtccag gaacaggtgg tggcg                    45

<210> SEQ ID NO 8
<211> LENGTH: 49
<212> TYPE: DNA
<213> ORGANISM: Artificial Sequence
<220> FEATURE:
<223> OTHER INFORMATION: Subcloning of cogGFP-attB2 forward primer

<400> SEQUENCE: 8
cgttcactgc cgtataggca gctaagaaat atggtgagca agggcgagg                49

<210> SEQ ID NO 9
<211> LENGTH: 47
<212> TYPE: DNA
<213> ORGANISM: Artificial Sequence
<220> FEATURE:
<223> OTHER INFORMATION: Subcloning of cogGFP-attB2 reverse primer

<400> SEQUENCE: 9
accactttgt acaagaaagc tgggtacttg tacagctcgt ccatgcc                  47

<210> SEQ ID NO 10
<211> LENGTH: 48
<212> TYPE: DNA
<213> ORGANISM: Artificial Sequence
<220> FEATURE:
<223> OTHER INFORMATION: Subcloning of cogRFP-attB2 forward primer

<400> SEQUENCE: 10
cgttcactgc cgtataggca gctaagaaat atggcctcct ccgagaac                 48

<210> SEQ ID NO 11
<211> LENGTH: 57
<212> TYPE: DNA
<213> ORGANISM: Artificial Sequence
<220> FEATURE:
<223> OTHER INFORMATION: Subcloning of cogFLuc-attB2 forward primer

<400> SEQUENCE: 11
cgttcactgc cgtataggca gctaagaaat atggttactg atgctaaaaa tattaag      57

<210> SEQ ID NO 12
<211> LENGTH: 45
<212> TYPE: DNA
<213> ORGANISM: Artificial Sequence
<220> FEATURE:
<223> OTHER INFORMATION: Subcloning of cogFLuc-attB2 reverse primer

<400> SEQUENCE: 12
gaccactttg tacaagaaag ctgggtctca cagcgatctt cctc                    45

<210> SEQ ID NO 13
<211> LENGTH: 44
<212> TYPE: DNA
<213> ORGANISM: Artificial Sequence
<220> FEATURE:
<223> OTHER INFORMATION: BP cloning of pDONR221-attB3-cogGFP/RFP/FLuc-
      attB2 forward primer

<400> SEQUENCE: 13
gacaactttg tataataaag ttggccgttc actgccgtat aggc                    44
```

<210> SEQ ID NO 14
<211> LENGTH: 37
<212> TYPE: DNA
<213> ORGANISM: Artificial Sequence
<220> FEATURE:
<223> OTHER INFORMATION: Infusion cloning of pTKan-pAct2-cogRFP-tNOS-
      p35S-attR1-GW-attR2 and amplification of pAct2 forward primer

<400> SEQUENCE: 14
ggggatcctc tagagggagt cgacaaaatt tagaacg                    37

<210> SEQ ID NO 15
<211> LENGTH: 44
<212> TYPE: DNA
<213> ORGANISM: Artificial Sequence
<220> FEATURE:
<223> OTHER INFORMATION: Infusion cloning of pTKan-pAct2-cogRFP-tNOS-
      p35S-attR1-GW-attR2 and amplification of pAct2 reverse primer

<400> SEQUENCE: 15
gcctatacgg cagtgaacgt tcaaagcgga gaggaaaata tatg            44

<210> SEQ ID NO 16
<211> LENGTH: 38
<212> TYPE: DNA
<213> ORGANISM: Artificial Sequence
<220> FEATURE:
<223> OTHER INFORMATION: Amplification of cogRFP reverse primer

<400> SEQUENCE: 16
tccgcggacg tcccgggccc gagcttgcat gccggtcg                   38

<210> SEQ ID NO 17
<211> LENGTH: 42
<212> TYPE: DNA
<213> ORGANISM: Artificial Sequence
<220> FEATURE:
<223> OTHER INFORMATION: Infusion cloning of pGCI into pDON-tG7-pGCI
      B4rB3r construct forward primer

<400> SEQUENCE: 17
tgtaccccgg gtaccaagct tgagtaaaga ttcagtaacc cg              42

<210> SEQ ID NO 18
<211> LENGTH: 46
<212> TYPE: DNA
<213> ORGANISM: Artificial Sequence
<220> FEATURE:
<223> OTHER INFORMATION: Infusion cloning of pGCI into pDON-tG7-pGCI
      B4rB3r construct reverse primer

<400> SEQUENCE: 18
tattatacaa agttgtccta ggatttcttg agtagtgatt ttgaag          46

<210> SEQ ID NO 19
<211> LENGTH: 38
<212> TYPE: DNA
<213> ORGANISM: Artificial Sequence
<220> FEATURE:
<223> OTHER INFORMATION: Infusion cloning of pGmUbi into pDON-tG7-pGmUbi
      B4rB3r construct forward primer

<400> SEQUENCE: 19
tgtaccccgg gtaccaagct tcagtgcagc gtgacccg                   38

```
<210> SEQ ID NO 20
<211> LENGTH: 43
<212> TYPE: DNA
<213> ORGANISM: Artificial Sequence
<220> FEATURE:
<223> OTHER INFORMATION: Infusion cloning of pGmUbi into pDON-tG7-pGmUbi
      B4rB3r construct reverse primer

<400> SEQUENCE: 20
tattatacaa agttgtccta ggggatcctc tagagtcgac ctg          43

<210> SEQ ID NO 21
<211> LENGTH: 18
<212> TYPE: DNA
<213> ORGANISM: Artificial Sequence
<220> FEATURE:
<223> OTHER INFORMATION: RT-PCR of cogGFP, primer spanning the cleavage
      site forward

<400> SEQUENCE: 21
ctcagcagct tcttctgc                                       18

<210> SEQ ID NO 22
<211> LENGTH: 18
<212> TYPE: DNA
<213> ORGANISM: Artificial Sequence
<220> FEATURE:
<223> OTHER INFORMATION: RT-PCR of cogGFP, primer spanning the cleavage
      site reverse

<400> SEQUENCE: 22
gacacgctga acttgtgg                                       18

<210> SEQ ID NO 23
<211> LENGTH: 20
<212> TYPE: DNA
<213> ORGANISM: Artificial Sequence
<220> FEATURE:
<223> OTHER INFORMATION: RT-PCR of cogGFP, primer downstream of the
      cleavage site forward

<400> SEQUENCE: 23
atatcatggc cgacaagcag                                     20

<210> SEQ ID NO 24
<211> LENGTH: 20
<212> TYPE: DNA
<213> ORGANISM: Artificial Sequence
<220> FEATURE:
<223> OTHER INFORMATION: RT-PCR of cogGFP, primer downstream of the
      cleavage site reverse

<400> SEQUENCE: 24
tctcgttggg gtctttgctc                                     20

<210> SEQ ID NO 25
<211> LENGTH: 20
<212> TYPE: DNA
<213> ORGANISM: Artificial Sequence
<220> FEATURE:
<223> OTHER INFORMATION: RT-PCR of CSY4 forward primer

<400> SEQUENCE: 25
agacccagag ttccctccag                                     20

<210> SEQ ID NO 26
<211> LENGTH: 20
```

```
<212> TYPE: DNA
<213> ORGANISM: Artificial Sequence
<220> FEATURE:
<223> OTHER INFORMATION: RT-PCR of CSY4 reverse primer

<400> SEQUENCE: 26
agccctaagg tcatctgctg                                          20

<210> SEQ ID NO 27
<211> LENGTH: 20
<212> TYPE: DNA
<213> ORGANISM: Artificial Sequence
<220> FEATURE:
<223> OTHER INFORMATION: RT-PCR and qPCR of cogRFP, primer spanning the
      cleavage site reverse

<400> SEQUENCE: 27
tcgatctcga actcgtggcc                                          20

<210> SEQ ID NO 28
<211> LENGTH: 21
<212> TYPE: DNA
<213> ORGANISM: Artificial Sequence
<220> FEATURE:
<223> OTHER INFORMATION: RT-PCR of cogRFP, primer downstream of the
      cleavage site forward

<400> SEQUENCE: 28
catcaagttg gacatcacct c                                        21

<210> SEQ ID NO 29
<211> LENGTH: 22
<212> TYPE: DNA
<213> ORGANISM: Artificial Sequence
<220> FEATURE:
<223> OTHER INFORMATION: RT-PCR of cogRFP, primer downstream of the
      cleavage site reverse

<400> SEQUENCE: 29
ccactttgta caagaaagct gg                                       22

<210> SEQ ID NO 30
<211> LENGTH: 22
<212> TYPE: DNA
<213> ORGANISM: Artificial Sequence
<220> FEATURE:
<223> OTHER INFORMATION: RT-PCR of EF1 forward primer

<400> SEQUENCE: 30
agggtccaac cctccttgag gc                                       22

<210> SEQ ID NO 31
<211> LENGTH: 20
<212> TYPE: DNA
<213> ORGANISM: Artificial Sequence
<220> FEATURE:
<223> OTHER INFORMATION: RT-PCR of EF1 reverse primer

<400> SEQUENCE: 31 gccccttttgg ctgggtcgtc                                         20

<210> SEQ ID NO 32
<211> LENGTH: 21
<212> TYPE: DNA
<213> ORGANISM: Artificial Sequence
<220> FEATURE:
<223> OTHER INFORMATION: RT-PCR of ND02 forward primer
```

```
<400> SEQUENCE: 32
caagttgacc gcaaatcctg t                                              21

<210> SEQ ID NO 33
<211> LENGTH: 20
<212> TYPE: DNA
<213> ORGANISM: Artificial Sequence
<220> FEATURE:
<223> OTHER INFORMATION: RT-PCR of ND02 reverse primer

<400> SEQUENCE: 33
ctgcttttcc ctgcaaccac                                                20

<210> SEQ ID NO 34
<211> LENGTH: 20
<212> TYPE: DNA
<213> ORGANISM: Artificial Sequence
<220> FEATURE:
<223> OTHER INFORMATION: RT-PCR of MZ1T forward primer

<400> SEQUENCE: 34
gcaaggggag atgcagctaa                                                20

<210> SEQ ID NO 35
<211> LENGTH: 20
<212> TYPE: DNA
<213> ORGANISM: Artificial Sequence
<220> FEATURE:
<223> OTHER INFORMATION: RT-PCR of MZ1T reverse primer

<400> SEQUENCE: 35
cactctctga gcaggccttc                                                20

<210> SEQ ID NO 36
<211> LENGTH: 22
<212> TYPE: DNA
<213> ORGANISM: Artificial Sequence
<220> FEATURE:
<223> OTHER INFORMATION: qPCR of KAN forward primer

<400> SEQUENCE: 36
atctcctgtc atctcacctt gc                                             22

<210> SEQ ID NO 37
<211> LENGTH: 20
<212> TYPE: DNA
<213> ORGANISM: Artificial Sequence
<220> FEATURE:
<223> OTHER INFORMATION: qPCR of KAN reverse primer

<400> SEQUENCE: 37
tttcgcttgg tggtcgaatg                                                20

<210> SEQ ID NO 38
<211> LENGTH: 20
<212> TYPE: DNA
<213> ORGANISM: Artificial Sequence
<220> FEATURE:
<223> OTHER INFORMATION: qPCR of CSY4 forward primer

<400> SEQUENCE: 38
agctttggtt gcacaaggtg                                                20

<210> SEQ ID NO 39
```

```
<211> LENGTH: 22
<212> TYPE: DNA
<213> ORGANISM: Artificial Sequence
<220> FEATURE:
<223> OTHER INFORMATION: qPCR of CSY4 reverse primer

<400> SEQUENCE: 39
aaagccctaa ggtcatctgc tg                                              22

<210> SEQ ID NO 40
<211> LENGTH: 20
<212> TYPE: DNA
<213> ORGANISM: Artificial Sequence
<220> FEATURE:
<223> OTHER INFORMATION: qPCR of cogGFP forward primer

<400> SEQUENCE: 40
taaagttggc cgttcactgc                                                 20

<210> SEQ ID NO 41
<211> LENGTH: 20
<212> TYPE: DNA
<213> ORGANISM: Artificial Sequence
<220> FEATURE:
<223> OTHER INFORMATION: qPCR of cogGFP reverse primer

<400> SEQUENCE: 41
aacttgtggc cgtttacgtc                                                 20

<210> SEQ ID NO 42
<211> LENGTH: 28
<212> TYPE: DNA
<213> ORGANISM: Lactobacillus delbrueckii

<400> SEQUENCE: 42
gtattcccca cgcaagtggg ggtgatcc                                        28

<210> SEQ ID NO 43
<211> LENGTH: 29
<212> TYPE: DNA
<213> ORGANISM: Thauera aminoaromatica

<400> SEQUENCE: 43
ggttcccccg cgtccgcggg gataggccc                                       29

<210> SEQ ID NO 44
<211> LENGTH: 29
<212> TYPE: DNA
<213> ORGANISM: Escherichia coli

<400> SEQUENCE: 44
gagttccccg cgccagcggg gataaaccg                                       29

<210> SEQ ID NO 45
<211> LENGTH: 27
<212> TYPE: DNA
<213> ORGANISM: Moraxella catarrhalis

<400> SEQUENCE: 45
ttctaagcga cctgtgcggt cgtgaag                                         27

<210> SEQ ID NO 46
<211> LENGTH: 28
<212> TYPE: DNA
<213> ORGANISM: Verrucosispora maris
```

<400> SEQUENCE: 46
ggatcacccc cgcgtgcgcg gggagcag                                28

<210> SEQ ID NO 47
<211> LENGTH: 37
<212> TYPE: DNA
<213> ORGANISM: Staphylococcus epidermidis

<400> SEQUENCE: 47
gttctcgtcc cctttcttc ggggtgggta tcgatcc                       37